US00RE46907E

(19) United States
(12) Reissued Patent
Huang et al.

(10) Patent Number: US RE46,907 E
(45) Date of Reissued Patent: Jun. 26, 2018

(54) SUPPRESSION OF CANCER GROWTH AND METASTASIS USING NORDIHYDROGUAIARETIC ACID DERIVATIVES WITH METABOLIC MODULATORS

(71) Applicant: THE JOHNS HOPKINS UNIVERSITY, Baltimore, MD (US)

(72) Inventors: Ru Chih C. Huang, Baltimore, MD (US); Kotohiko Kimura, Baltimore, MD (US)

(73) Assignee: The Johns Hopkins University, Baltimore, MD (US)

(21) Appl. No.: 15/725,624

(22) Filed: Oct. 5, 2017

Related U.S. Patent Documents

Reissue of:
(64) Patent No.: 9,149,526
Issued: Oct. 6, 2015
Appl. No.: 12/812,196
PCT Filed: Jan. 8, 2009
PCT No.: PCT/US2009/030459
§ 371 (c)(1),
(2) Date: Sep. 30, 2010
PCT Pub. No.: WO2009/089366
PCT Pub. Date: Jul. 16, 2009

U.S. Applications:
(60) Provisional application No. 61/191,827, filed on Sep. 12, 2008, provisional application No. 61/010,371, filed on Jan. 8, 2008.

(51) Int. Cl.
*A61K 31/03* (2006.01)
*A61K 45/06* (2006.01)

(52) U.S. Cl.
CPC ..... *A61K 45/06* (2013.01); *A61K 31/03* (2013.01)

(58) Field of Classification Search
CPC ..... A61K 31/03; A61K 45/06
See application file for complete search history.

(56) References Cited

U.S. PATENT DOCUMENTS

| | | | | |
|---|---|---|---|---|
| 4,530,844 | A | 7/1985 | Smerbeck et al. | |
| 9,101,567 | B2 * | 8/2015 | Huang | A61K 31/553 |
| 2007/0099847 | A1 | 5/2007 | Goldfine et al. | |
| 2013/0053335 | A1 * | 2/2013 | Huang et al. | 514/25 |

FOREIGN PATENT DOCUMENTS

| | | | |
|---|---|---|---|
| WO | WO-9500129 | A1 | 1/1995 |
| WO | WO-03090681 | A2 | 11/2003 |
| WO | WO-03103583 | A2 | 12/2003 |
| WO | WO-2006/041902 | A2 | 4/2006 |

OTHER PUBLICATIONS

Wiesenthal, (Human Tumor Assay Journal, on-line at (http://weisenthal.org/synergy1.htm, Mar. 14, 2012).*
Berenbaum (Clin exp Immunol, 1997, 28:1-18).*
Santos et al. (Biochemical Pharmacology, 2003, 65: 1035-1041).*
Altundag, K. et al. "Overcoming Trastuzumab Resistance with nordihydroguaiaretic acid?" Breast Cancer research a Treatment 2006, 96(3), 301, ISSN:0167-6806.
Brennan, P. et al. "Inhibition of Nuclear Factor kB by Direct Modification in Whole Cells-Mechanism of Action Nordihydroguaiaritic Acid,Cucumin and Thiol Modifiers" Biochemical Pharmacology 1998, 55(7), 965-973, ISSN: 0006-2952.
International Search Report and Written Opinion of International Application No. PCT/US2009/030459 filed Jan. 8, 2009.
Chih-Chuan Chang etal., "Reversal of Multidrug resistance by two nordihydroguaiaretic acid derivatices, M4N and Maltose-M3N, and their use in combination with doxorubicin or paclitaxel", Cancer Chemotherapy and Pharmacology, Springer, Berlin, DE, vol. 58, No. 5, Mar. 17, 2006 pp. 640-653.
Dancey et al., "Strategies for optimizing combinations of molecular targeted anticancer agents", Nature Reviews Drug Discovery, vol. 5, Aug. 31, 2006, pp. 649-659.
Supplementary European Search Report dated May 19, 2011 for Application No. EP 09 70 1300.
Acs et al., 2000. Effect of a tyrosine 155 to phenylalanine mutation of protein kinase C6 on the proliferation and tumorigenic properties of NIH 3T3 fibroblasts. Carcinogenesis 21:887-891.
Aldinucci et al., 2007. Hypoxia affects the physiological behavior of rat cortical synaptosomes. Free Radic. Biol. Med. 42:1749-1756.
Ambrosini et al., 1997. A novel anti-apoptosis gene, surviving, expressed in cancer and lymphoma. Nat. Med. 3:917-921.
Aslakson et al., 1992. Selective events in the metastatic process defined by analysis of the sequential dissemination of subpopulation of a mouse mammary tumor. Cancer Res: 52:1399-1405.
Baek et al., 2001. Role of protein kinase Cd in transmitting hypoxia signal to HSF and HIF-1. J. Cell. Phys. 188:223-235.
Berrie, C.P. 2001. Phosphoinisitide 3-kinase inhibition in cancer treatment. Expert Opin. Investg. Drugs, 10: 1085-98.
Blass et al., 2002. Tyrosine phosphorylation of protein kinase Co is essential for its apoptotic effect in response to Etoposide. Mol. Cell. Biol. 22:182-195.
Bonnet et al., 2007. A mitochondria-$K^{\pm}$ channel axis is suppressed in cancer and its normalization promotes apoptosis and inhibits cancer growth. Cancer Cell, 11:37-51.
Brodie et al., 2003. Regulation of cell apoptosis by protein kinase CS. Apoptosis 8:19-27.
Chang et al., 2003. Signal transduction mediated by the Ras/Raf/MEK/ERK pathway from cytokine receptors to transcription factors: potential targeting for therapeutic intervention. Leukemia 17:1263-1293.

(Continued)

*Primary Examiner* — Jerry D Johnson
(74) *Attorney, Agent, or Firm* — John Hopkins Technology Ventures

(57) ABSTRACT

Disclosed is a composition comprising a derivative of NDGA and at least one metabolic modulator. The composition can be in a unit dose form or kit. The composition can comprise at least two metabolic modulators. Also disclosed are methods for achieving cytotoxicity, particularly of rapidly dividing cells such as cancer, by administering a composition of the invention. In various embodiments of the invention subjects with cancer achieve prolonged survival and/or diminution in the size of their malignancies and cancer metastasis.

14 Claims, 16 Drawing Sheets

(56) References Cited

OTHER PUBLICATIONS

Chang et al., 2004. Tetra-O-methyl nordihydroguaiaretic acid induces growth arrest and cellular apoptosis by inhibiting Cdc2 and surviving expression. Proc. Natl. Acad. Sci. U.S.A. 101:13239-13244.
Chang et al., 2006. Reversal of multidrug resistance by two nordihydroguaiaretic acid derivatives, M4N and maltose-M3N, and their use in combination with doxorubicin or paclitaxel. Cancer Chemotherapy Pharmacol. 58:640-653.
Chen et al., 1998. Antiviral activities of methylated nordihydroguaiaretic acids. 2. Targeting *Helpes simplex virus* replication by the mutation insensitive transcription inhibitor tetra-O-methyl-NDGA. J. Med. Chem. 41:3001-3007.
Clavijo et al., 2007. Protein kinase CO-dependent and -independent signaling in genotoxic response to treatment of desferroxamine, a hypoxia-mimetic agent. Am. J. Physiol. Cell Physiol. 292:C2150-C2160.
Conte et al., 2004. The role of PKC and PKC in the neonatal rat colon in response to hypoxia challenge. Pediatric Res. 55:27-33.
Craigo et al., 2000. Inhibition of human papillomavirus type 16 gene expression by nordihydroguaiaretic acid plant lignan derivatives. Antiviral Res. 47:19-28.
Cully et al., 2006. Beyond PTEN mutations: the PI3K pathway as an integrator of multiple inputs during tumorigenesis. Nature Rev. Cancer, 6:184-192.
Da Rocha et al., 2002. Targeting protein kinase C: New therapeutic opportunities against high-grade malignant gliomas? The Oncologist 7: 17-33.
Dalton, S. 1992. Cell cycle regulation of the human cdc2 gene. The EMBO J. 11:1797-1804.
Davies et al., 2000. Specificity and mechanism of action of some commonly used protein kinase inhibitors. Biochem. J. 351 (Pt 1):95-105.
Deveraux et al., 1999. IAP family proteins-suppressors of apoptosis. Genes Dev. 13:239-252.
Devries et al., 2002. Nuclear import of PKC5 is required for apoptosis: identification of a novel nuclear import sequence. The EMBO J. 21:6050-6060.
Devries-Seimon et al., 2007. Induction of apoptosis is driven by nuclear retention of protein kinase C delta. J. Biol. Chem. 282:22307-22314.
Eckhardt et al., 2005. Genomic analysis of a spontaneous model of breast cancer metastasis to bone reveals a role for the extracelluar matrix. Mol. Cancer Res. 3:1-13.
Emoto et al., 1995. Proteolytic activation of protein kinase C 5 by an ICE-like protease in apoptotic cells. The EMBO J. 14:6148-6156.
Faivre et al., 2006. New paradigms in anticancer therapy: targeting multiple signaling pathways with kinase inhibitors. Semin. Oncol. 33:407-420.
Fang et al., 1991. Evidence that the GI-S and G2-M transitions are controlled by different cdc2 proteins in higher eukaryotes. Cell 66:731-742.
Fukunaga et al., 2001. UV-induced Tyrosine phosphorylation of PKC8 and promotion of apoptosis in the HaCaT cell line. Biochem. Biophys. Res. Comm. 289:573-579.
Ghayur et al., 1996. Proteolytic activation of protein kinase C delta by an ICE/CED 3-like protease induces characteristics of apoptosis. J. Exp. Med. 184:2399-2404.
Gnabre et al., 1995. Inhibition of human immunodeficiency virus type 1 transcription and replication by DNA sequence-selective plant lignans. Proc. Natl. Acad. Sci. U.S.A. 92:11239-11243.
Gordan et al., 2007 Hypoxia-inducible factors: central regulators of the tumor phenotype. Curr. Opin. Genet. Dev. 17:71-77.
Grossman, et al., 1999. Expression and targeting of the apoptosis inhibitor, survivin, in human melanoma. J. Invest. Dermatol. 113:1076-1081.
Gschwendt et al., 1994. Rottlerin, a novel protein kinase inhibitor. Biochem. Biophys. Res. Comm. 199:93-98.
Gupta et al., 2003. Radiation sensitization of human cancer cells in vivo by inhibiting the activity of PI3K using Ly294002. Int. J. Radiation Oncol. Biol. Phys. 56:846-853.
Heller et al., 2001. Tetra-O-methyl nordihydroguaiaretic acid induces G2 arrest in mammary cells and exhibits tumoricidal activity in vivo. Cancer Res. 61:5499-5504.
Hu et al., 2000. In vivo and in vitro ovarian carcinoma growth inhibition by a hosphatidylinositol 3-kinase inhibitor (LY294002). Clin. Cancer Res. 6:880-886.
Hwu et al., 1998. Antiviral activities of methylated nordihydroguaiaretic acids. 1. Synthesis, structure identification, and inhibition of tat-regulated HIV transactivation. J. Med. Chem. 41:2994-3000.
Jackson et al., 2004. The enigmatic kinase CS: complex roles in cell proliferation and survival. FASEB J. 18:627-636.
Kao et al., 1999. Muschel. P34(Cdc2) kinase activity is excluded from the nucleus during the radiation-induced G(2) arrest in HeLa cells. J. Biol. Chem. 274:34779-34784.
Kaul et al., 2005 Tyrosine Phosphorylation Regulates the Proteolytic Activation of Protein Kinase C in Dopaminergic Neuronal Cells. J. Biol. Chem. 280:28721-30.
Kikkawa et al., 1983. Protein kinase C as a possible receptor protein of tumor-promoting phorbol esters. J. Biol. Chem. 258:11442-11445.
Kikkawa et al., 1989. The protein kinase C family: heterogeneity and its implications. Annu. Rev. Biochem. 58:31-44.
Kim et al., 2005. Rottlerin sensitized gloma cells to TRAIL-induced apoptosis by inhibition of Cdc-2 and the subsequent downregulation of surviving and XIAP. Oncogene 24:838-849.
Kroemer et al., 2005. Caspase-independent cell death. Nature Med. 11:725-730.
Kroemer et al., 2007. Mitochondrial membrane permeabilization in cell death. Physiol. Rev. 87:99-163.
Le Good et al., 1998. Protein kinase C isotypes controlled by phosphoinositide 3-kinase through the protein kinase PDK1 . Science 281:2042-2045.
Li et al., 1999. Protein kinase C8 targets mitochondria, alters mitochondrial membrane potential, and induces apoptosis in normal and neoplastic keratiocytes when overexpressed by an adenovirus vector. Mole. Cell. Biol. 19:8547-8558.
Li et al., 2001. Tumor cell death induced by topoisomerase-targeting drugs. Ann. Rev. Pharmacol. Toxicol. 41:53-77.
Liu et al., 2002. Phosphorylation of the protein kinase C-theta activation loop and hydrophobic motif regulates its kinase activity, but only activation loop phosphorylation is critical to in vivo nuclear-facor—KB induction. Biochem. J. 361:255-265.
Liu et al., 2006. Independence of protein kinase C-8 activity from activation loop phosphorylation. Structural basis and altered functions in cells. J. Biol. Chem. 281:12102-12111.
Lopez et al., 2007. The anticancer activity of the transcription inhibitor terameprocol (meso-tetra-O-methyl nordihydroguaiaretic acid) formulated for systemic administration. Anti-Cancer Drugs 18:933-939.
MacKintosh, C. 2004. Dynamic interactions between 14-3-3 proteins and phosphoproteins regulate diverse cellular processes. Biochem, J. 381:329-342.
Manka et al., 2005. Bcl-2/adenovirus EI B 19kDa interacting protein-3 knockdown enables growth of breast cancer metastases in the lung, liver, and bone. Cancer Res. 15:11689-11693.
Manning et al., 2007. Akt/PkB signaling: Navigating downstream. Cell 129:1261-1274.
Megha et al., 1999. Expression of the G2-M checkpoint regulators cyclin B1 and P34CDC2 in breast cancer: a correlation with cellular kinetics. Anticancer Res. 19:163-169.
Melillo, G., 2007. Targeting hypoxia cell signaling for cancer therapy. 2007. Cancer Metastasis Rev. 26: 341-352.
Morgan, D.O. 1995. Principles of cdk regulation. Nature 374:131-134.
Morgensztern et al., 2005. PI3KJAkt/mTOR pathway as a target for cancer therapy. Anticancer Drugs. 16:797-803.

(56) References Cited

OTHER PUBLICATIONS

Murray, A.W. 1992. Creative blocks: cell-cycle checkpoints and feedback controls. Nature 359: 599-604.
Newton, A.C. 2003. Regulation of the ABC kinases by phosphorylation: protein kinase C as a paradigm. Biochem J. 370 (Pt 2):361-371.
O'Connor et al., 2000. Regulation of apoptosis at cell division by p34cdc2 phosphorylation of surviving. Proc. Natl. Acad. Sci. U.S.A. 97:13103-13107.
Osaki et al., 2004. PI3K-Akt pathway:Its function and alterations in human cancer. Apoptosis, 9:667-676.
Parcellier et al., 2008. PKB and the mitochondria: AKTing on apoptosis. Cellular Signal. 20:21-30.
Parekh et al., 2000. (31-Integrin and PTEN control the phosphorylation of protein kinase C. Biochem. J. 352:425-433.
Parekh et al., 2000. Multiple pathways control protein kinase C phosphorylation. EMBO J. 19:496-503.
Park et al., 2005. Systemic treatment with tetra-O-methyl nordihydroguaiaretic acid suppresses the growth of human xenograft tumors. Clin. Cancer Res. 11:4601-4609.
Pulaski et al., 1998. Reduction of established spontaneous mammary carcinoma metastasis following immunotherapy with major histocompatibility complex class II and B7.1. Cancer Res. 58:1486-1493.
Reusch et al., 2001. Regulation of Raf by Akt controls growth and differentiation in vascular smooth muscle cells. J. Biol. Chem. 276:33630-33637.
Ringshausen et al., 2006. Mechanisms of apoptosis-induction by rottlerin: therapeutic implications for B-CLL. Leukemia 20:514-520.
Rybin et al., 2003. Cross-regulation of novel protein kinase C (PKC) isoform function in cardiomyocytes. J. Biol. Chem. 278:14555-14564.
Semba et al., 2002. The in vitro and in vivo effects of 2-(2-morpholinyl)-8-phenyl-chromone (LY294002), a specific inhibition of phosphatidylinositol 3'-kinase, in human colon cancer cells. Clin. Cancer Res. 8:1957-1963.
Serova et al., 2006. Preclinical and clinical development of novel agents that target the protein kinase C family. Seminars in Oncology 33:466-478.
Shizukuda et al., 1999. Downregulation of protein kinase C8 activity enhances endothelial cell adaptation to hypoxia. Circulation 100:1909-1916.
Stein, R.C. 2001. Prospects for phosphoinositide 3-kinase inhibition as a cancer treatment. Endocr. Reat. Cancer. 8: 237-48.
Steinberg, S.F. 2004. Distinctive activation mechanisms and functions for protein kinase C8. Biochem. J. 384:449-459.
Stempka et al., 1997. Phosphorylation of protein kinase C8 (PKC5) at Threonine 505 is not a prerequisite for enzymatic activity. J. Biol. Chem. 272:6805-6811.
Stempka et al., 1999. Requirements of protine kinase C8 for catalytic function. J. Biol. Chem. 274:8866-8892.
Tamm et al., 1998. IAP-family protein surviving inhibits caspase activity and apoptosis induced by Fas (CD95), Bax, caspases, and anticancer drugs. Cancer Res. 58:5315-5320.
Tillman et al., 2003: Rottlerin sensitizes colon carcinoma cells to tumor necrosis factor-related apoptosis-inducing ligand-induced apoptosis via uncoupling of the mitochondria independent of protein kinase C. Cancer Res. 63:5118-5125.
Vander Haar et al., 2007. Insulin signaling to mTOR mediated by the Akt/PKB substrate PRAS40. Nature Cell Biol. 9:316-323.
Wang et al., 1999. High-malignancy orthotopic nude mouse model of human prostate cancer LNCaP. The Prostate 39:182-186.
Watanabe et al., 1992. Cell division arrest induced by phorbol ester in CHO cells overexpressing protein kinase CS subspecies. Proc. Natl. Acad. Sci. U.S.A. 89:10159-10163.
Wouters et al., 2007. Review: implications of in vitro research on the effect of radiotherapy and chemotherapy under hypoxic conditions. Oncologists 12:690-712.
Yang et al., 2004. Twist, a master regulator of morphogenesis, plays an essential role in tumor metastasis. Cell 117: 927-939.
Yeh et al., 2006. A microfluidic-FCS platform for investigation on the dissociation of Spl-DNA complex by doxorubicin. Nucleic Acids Res. 34:e144.
Yoshida et al., 2006. Protein kinase C S activates topoisomerase IIa to induce apoptotic cell death in response to DNA damage. Mol. Cell. Biol. 26:3414-3431.

* cited by examiner

A

B

SUPPRESSION OF CANCER GROWTH AND METASTASIS USING NORDIHYDROGUAIARETIC ACID DERIVATIVES WITH METABOLIC MODULATORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

[This is a U.S. national stage application of PCT /US2009/030459, filed Jan. 8, 2009, which claims priority to U.S. Provisional Patent Application 61/010,371, filed Jan. 8, 2008, and U.S. Provisional Patent Application 61/191,827, filed Sep. 12, 2008, each of which is incorporated by reference in its entirety.] *This application is a reissue of a U.S. Pat. No. 9,149,526, U.S. Ser. No. 12/812,196, filed Sep. 30, 2010, which was a 35 U.S.C. § 371 U.S. national entry of International Application PCT/US2009/030459, having an international filing date of Jan. 8, 2009, which claims the benefit of U.S. Provisional Application Nos. 61/010,371, filed Jan. 8, 2008, and 61/191,827, filed Sep. 12, 2008, the content of each of the aforementioned applications is herein incorporated by reference in their entireties.*

FIELD OF THE INVENTION

This invention relates to the use of nordihydroguaiaretic acid derivatives together with one or more metabolic modulators to treat cancer, prevent metastasis, and prolong the life of a mammal afflicted with a tumor.

BACKGROUND

Carcinogenesis is a multistage event affected by a variety of genetic and epigenetic factors and is typified by the outbreak of uncontrolled cell growth originated from different tissues. A universal goal for anticancer research lies in the development of a clinical treatment that is highly effective in curtailment of tumor growth, non-toxic to the host, and is affordable for most patients. Drugs that inhibit targets that are unique to dividing cells, particularly cells dividing in an uncontrolled manner, are an ideal paradigm for chemotherapeutic agents, the greater the specificity to cells that are dividing in an uncontrolled manner the lower the risk of attendant side effects.

Under normal conditions cells in our bodies are involved in a balanced system of programmed growth, division, rest, and death. The regulation of these cellular pathways is essential in order to maintain tissue viability and bodily health. The transition of a healthy cell to a precancerous or cancerous cell is initiated by the disruption of these regulatory pathways. Cancer cells then redirect the cellular systems to allow for uncontrolled cell growth, replication, and/or resistance to programmed cell death (apoptosis).

Caspases are one means of inducing apoptosis. Apoptosis is regulated by the inhibitor of apoptosis protein (IAP) family of proteins, through their inhibition of caspase-induced cell death. One of the IAP family members, survivin, is overexpressed in pre-cancerous and cancerous cells, and rarely found in healthy adult cells. By their high survivin expression, tumor cells are prevented from entering the caspase-induced cell death pathway that would lead to their destruction. Survivin is one of the targets currently being tested for anticancer therapy.

Another mechanism by which tumor cells grow uncontrollably is by deregulating their cell cycle process. Cdc2 (cyclin-dependent kinase-1) is one of several kinase proteins controlling cell division and is frequently de-regulated in cancer cells. Cdc2 is also involved in the activation of survivin. In addition, growing tumors require a constant supply of essential nutrients and oxygen. Cancer cells achieve their nutrient needs by secreting Vascular Endothelial Growth Factor (VEGF) to induce new blood vessel formation within the tumor mass.

Proteins such as those mentioned above are involved in the regulation of the signaling pathways that control cell growth, division and death. Some of these proteins are significantly altered in cancer cells. The process of converting the gene sequence on DNA to an RNA message (a process called transcription) that can then be converted to protein (a process called translation) is essential to the regulation of protein production.

Cells pass through many checkpoints as they proceed through the cell cycle. Certain criteria must be met in order to pass each of these checkpoints. In the G2/M transition, the most essential regulator is the cyclin-dependent kinase CDC2. This kinase binds tightly to the regulatory protein cyclin B, and this complex, also called the maturation promoting factor (MPF), is responsible for stimulating a myriad of events that lead to the cell's entry into early prophase (1). Not surprisingly, the loss or deactivation of either component of the MPF will block cellular progression out of G2.

The expression and activity of the MPF is regulated at different levels. Cyclin B protein levels slowly rise through the G1 and S phases of the cell cycle, peak during the G2 to M phase transition, and drop sharply during mitosis (2). The CDC2 protein, on the other hand, is always present during the cell cycle, although levels rise slightly in the last stages of the G2 phase (3). The activity of the protein is dependent on the association with the appropriate cyclin, as well as on the dephosphorylation of its inhibitory sites by the phosphatase CDC25C (4, 5). It has been shown that the failure of this dephosphorylation initiates G2 arrest in response to DNA damage by radiation or chemical action. Recent evidence also suggests that any remaining active CDC2 may be transported outside the nucleus following DNA damage (6).

Survivin is an inhibitor of apoptosis that is abundantly expressed in many human cancers (7), but not in normal adult human tissue, and is considered a possible modulator of the terminal effector phase of cell death/survival. (8). Survivin is expressed in $G_2$-M in a cell cycle-dependent manner, binding directly to mitotic spindle microtubules. It appears that survivin phosphorylation on Thr34 may be required to maintain cell viability at cell division (9), and expression of a phosphorylation-defective survivin mutant has been shown to trigger apoptosis in several human melanoma cell lines (10), Phosphorylated survivin acts on the caspase pathway to suppress the formation of caspase-3 and caspase-9, thereby inhibiting apoptosis. (11) Although compounds that reduce the expression of survivin will be expected to increase the rate of apoptosis and cell death, CDC-2 has been shown to be necessary for survivin phosphorylation (9). In addition, the activation of caspases is a time-dependent event as it occurs slowly, quite often inefficiently.

A number of naturally occurring derivatives of the plant lignan nordihydroguaiaretic acid (NDGA) have been shown to block viral replication through the inhibition of viral transcription. NDGA is extracted from the resin of the leaves of Larrea tridentata, a desert bush indigenous to the southwestern US and Mexico. Derivatives of NDGA can inhibit the production of HIV (12, 13), HSV (14), and HPV transcripts (15) by the deactivation of their Sp1-dependent promoters. Isolation and purification of plant lignans, however, is labor intensive and costly. In anticipation of the possible clinical use of plant lignans in controlling Sp1-regulated viral and tumor growth in humans, nine different methylated NDGA activities were synthesized chemically using unmethylated NDGA as the parent substrate in large quantities with low cost (12).

Nordihydroguaiaretic acid ($M_4N$, EM1421, Terameprocol), is the synthetic tetra-methylated derivative of nordihydroguaiaretic acid (tetra-O-methyl nordihydroguaiaretic acid, abbreviated as $M_4N$), The chemical structure of $M_4N$ was designed to make it pharmacologically distinct from NDGA. $M_4N$ has been shown to possess antiviral (12, 14) and anti-cancer (16) activities in cultured cells, in mouse models (16, 17), and in human xenografts in nude mice (18). $M_4N$ causes cell cycle arrest at the G2 phase of the cell cycle probably by suppressing Sp-1 regulated cdk expression (16, 19). $M_4N$ has been in Phase I clinical trials in patients by intravenous infusion (CLINICAL TRIALS.GOV, A service of U.S. NIH).

Nordihydroguaiaretic acid (NDGA) derivatives such as $M_4N$ suppress Sp1 regulated transcription of viral genes, by deactivation of Sp1-dependent promoters. SP1 also affects expression of many growth-related genes. Cdc2 (also referred to as CDK1) and cyclin B interact to allow cells to move from the G2 phase of cell division to mitosis. $M_4N$ blocks the transcription of Cdc2, and thus blocks cell division. The Sp1 protein on promoter of CDC2 chromatin is replaced following $M_4N$ treatment in vivo.

$M_4N$ is able to induce cell cycle arrest in mammalian cell lines; $M_4N$ is a transcription inhibitor. It selectively reduces transcription of growth related genes that have promoters controlled by the Sp1 factor, such as cdc2, survivin and VEGP. By blocking production of cdc2, and VEGF, $M_4N$ inhibits tumor growth and starves tumors by restricting growth of their blood supply.

$M_4N$ has been shown to arrest growth of a variety of human cells in vitro, the majority of which are part of the NCI panel of 60 cancer cell lines, including solid tumor cell lines (bladder, breast, colorectal, liver, lung, ovarian, pancreatic, prostate and cervical carcinomas), and erythroleukemia cells. In vivo, $M_4N$ also decreases tumor cell growth and exhibits antitumor activity in a large number of tumor xenograft models, including human bladder, breast, colorectal liver, ovarian, pancreatic, prostate and cervical carcinomas, and erythroleukemia, without apparent toxicity. $M_4N$ has a broad spectrum of activity in anti-cancer therapy, having affects on Cdc2, HIF-1α, MDR1, VEGF and survivin. For example, $M_4N$ induces apoptosis and reduces cdc2 protein levels in human oral cancers. $M_4N$ also appears to reduce survivin levels in these cancers. Administered systemically, $M_4N$ was also shown to inhibit xenografted human tumors MCF-7, Hep3b, LNCaP, HT-29, and K562. Although none of the xenograft tumors were fully eradicated.

$M_4N$ does not appear toxic to animals. For example, $M_4N$ retention in mouse organs following oral administration has been studied after short term and long term feeding, the results showed essentially no toxic effects even at concentrations high as 906 μg/g of tissue. On daily (1 mg/day) IV injection of $M_4N$ for days, $M_4N$ accumulated in blood and tumors to levels above 1 mM in nude mice carrying human tumor xenografts.

By use of gene array studies with 9600 expressed genes. Applicants previously found products of most Sp1 regulated genes remained at similar levels, and not affected by the drug treatment of cervical cancer cells C3 in culture.

$M_4N$ has some favorable therapeutic qualities, in that it exhibits efficacy against several tumors, by inhibiting cell growth. However, in human clinical trials, treatment with $M_4N$ does not generally eradicate disease, and upon cessation of treatment with $M_4N$ tumors are capable of growing back. Accordingly, there is a need to identify ways to boost the efficacy of the $M_4N$ when the type of cancer is aggressive, metastatic or when $M_4N$ as a single drug in low concentration is not enough to induce rapid apoptosis of such type of cancers.

This application claims priority to U.S. Provisional Patent Application 60/010,371, filed Jan. 8, 2008, and U.S. Provisional Patent Application 61/191,827, filed Sep. 12, 2008, each of which is incorporated by reference in its entirety.

SUMMARY

As set forth herein, $M_4N$ and related derivatives of nordihydroguaiaretic acid have been used in combination with metabolic inhibitors to produce excellent results in tumor treatment, including prolonged patient survival as well as cytotoxicity to malignant cells.

Accordingly, it is one object to provide a pharmaceutical composition comprising an effective amount of nordihydroguaiaretic acid (NDGA) or a derivative thereof of formula I:

(I)

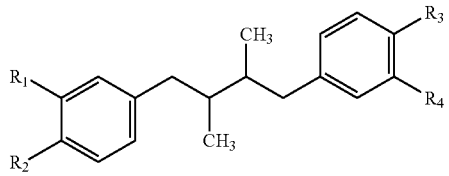

wherein $R_1$, $R_2$, $R_3$ and $R_4$ independently represent hydroxy, a straight or branched chain lower alkyl or alkoxy, an amino acid residue, a substituted amino acid residue, a nitrogen-containing 5- or 6-membered heterocyclic ring or a saccharide residue; the amino acid residue, substituted amino acid residue, nitrogen-containing 5 or 6 membered heterocyclic ring or saccharide residue being optionally joined to the phenyl ring by a linker of an oxygen atom and 1-10 carbon atoms, and an effective amount of a metabolic modulator.

In one specific embodiment, the pharmaceutical composition comprises the NDGA derivative [tetra-o-methyl] *tetra-O-methyl* nordihydroguaiaretic acid ($M_4N$). In another specific embodiment, the pharmaceutical composition comprises the NDGA derivative maltose $M_3N$ (90). In other specific embodiments, $R_1$, $R_2$, $R_3$ and $R_4$ are identical and represent straight or branched chain lower alkoxy groups or naturally occurring amino acid residues.

The metabolic modulator can be selected, for example from the group consisting of an inhibitor of the PDK-1/PI3K/AKT pathway, an inhibitor of the PKCδ/topoisomerase IIα pathway, an inhibitor of mitochondrial permeability transition, and an inhibitor of the mitogen-activated protein kinase (MAPK/RAS) pathway, or any other metabolic modulators which can systematically induce translocation of phosphorylated PCKδ to the nucleus of tumor cells. Examples of such metabolic inhibitors are Ly294002, etoposide, Rottlerin, dichloroacetate, cetuximab, trastuzumab, bevacizumab and rapamyein.

In certain preferred embodiments, the metabolic inhibitor is etoposide, rapamycin, rottlerin and/or water soluble derivatives thereof, such as temsirolimus, everolimus and other selected molecular targeting agents in clinical development (Nature Reviews Drug Discovery vol 5, p 650, 2006).

Also provided is a method of treating a tumor, comprising administering to a mammal in need of treatment an effective amount of the above-described pharmaceutical composition. The mammal can be any mammal afflicted with a tumor amenable to treatment, for example a human, nonhuman primate, cat, dog, mouse, etc. The tumor may be a solid or hematological tumor, benign or malignant (metastatic or non-metastatic), such as, for example, breast, liver, prostate, cervical, ovarian, colon, brain, pancreatic, bladder esophagus, gut, head and neck, kidney, melanoma, stomach, testes, thyroid, uterine and lung cancers, leukemias and lymphomas, such as acute myelogenous leukemia, acute or chronic lymphocytic leukemia, Hodgkin's and non-Hodgkin lymphoma, and myelomas. Persons of skill in the art will be able to determine by routine experimentation the types of tumors that are amenable to treatment. The treatment method is particularly suitable for treatment of metastatic and non-metastatic cancer.

Also provided is a method of preventing or inhibiting tumor growth in an animal, said method comprising administering an effective amount of nordihydroguaiaretic acid (NDGA) or a derivative thereof of formula I:

(I)

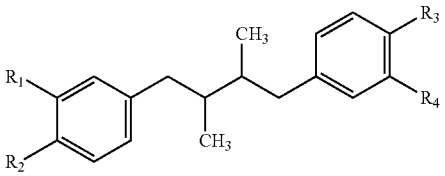

wherein $R_1$, $R_2$, $R_3$ and $R_4$ independently represent hydroxy, a straight or branched chain lower alkyl or alkoxy, an amino acid residue, a substituted amino acid residue, a nitrogen-containing 5- or 6-membered heterocyclic ring or a saccharide residue; the amino acid residue, substituted amino acid residue, nitrogen-containing 5 or 6 membered heterocyclic ring or saccharide residue being optionally joined to the phenyl ring by a linker of an oxygen atom and 1-10 carbon atoms, and an effective amount of a metabolic modulator.

In one specific embodiment, the NDGA derivative is [tetra-o-methyl] *tetra-O-methyl* nordihydroguaiaretic acid ($M_4N$). In another specific embodiment, the NDGA derivative is maltose $M_3N$ (90). In other specific embodiments, $R_1$, $R_2$, $R_3$ and $R_4$ are identical and represent straight or branched chain lower alkoxy groups or naturally occurring amino acid residues.

The mammal can be any mammal afflicted with a tumor amenable to treatment, for example a human, nonhuman primate, cat, dog, mouse, etc. The metabolic inhibitor is selected from the group consisting of an inhibitor of the PDK-1/PI3K/AKT pathway, an inhibitor of the PKCδ/topoisomerase IIα pathway, an inhibitor of mitochondrial permeability transition, and an inhibitor of the mitogen-activated protein kinase (MAPK/RAS) pathway. For example, the metabolic inhibitor is selected from the group consisting of Ly294002, etoposide, Rottlerin, dichloroacetate, cetuximab, trastuzumab, bevacizumab and rapamycin. Etoposide, rapamycin, and water soluble derivatives thereof are expected to be particularly effective.

The tumor may be a solid or hematological tumor, benign or malignant (metastatic or nonmetastatic), such as, for example, breast, prostate, cervical, ovarian, colon, brain, pancreatic and lung cancers, leukemias and lymphomas, and others mentioned hereinabove. Persons of skill in the art will be able to determine by routine experimentation the types of tumors that are amenable to treatment. The treatment method is particularly suitable for treatment of metastatic and non-metastatic cancer.

Also provided is a method of preventing tumor metastasis in a mammal, said method comprising administering an effective amount of nordihydroguaiaretic acid (NDGA) or a derivative thereof of formula I:

(I)

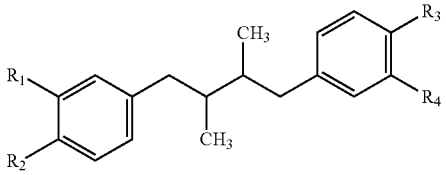

wherein $R_1$, $R_2$, $R_3$ and $R_4$ independently represent hydroxy, a straight or branched chain lower alkyl or alkoxy, an amino acid residue, a substituted amino acid residue and a saccharide residue; the amino acid residue, substituted amino acid residue or saccharide residue being optionally joined to the phenyl ring by a linker of an oxygen atom and 1-10 carbon atoms;

and an effective amount of a metabolic modulator.

In one specific embodiment, the NDGA derivative is [tetra-o-methyl] *tetra-O-methyl* nordihydroguaiaretic acid ($M_4N$)[.]. In another specific embodiment, the NDGA derivative is maltose $M_3N$ (90). In other specific embodiments, $R_1$, $R_2$, $R_3$ and $R_4$ are identical and represent straight or branched chain lower alkoxy groups or naturally occurring amino acid residues.

The mammal can be any mammal afflicted with a tumor amenable to treatment, for example a human, nonhuman primate, cat, dog, mouse, etc. The metabolic inhibitor is selected from the group consisting of an inhibitor of the PDK-1/PI3K/AKT pathway, an inhibitor of the PKCδ/topoisomerase IIα pathway, an inhibitor of mitochondrial permeability transition, and an inhibitor of the mitogen-activated protein kinase (MAPK/RAS) pathway. For example, the metabolic inhibitor is selected from the group consisting of Ly294002, etoposide, Rottlerin, dichloroacetate, cetuximab, trastuzumab, bevaeizumab and rapamycin, Etoposide, rapamycin, and water soluble derivatives thereof are expected to be particularly effective.

The tumor may be a solid or hematological tumor, such as, for example, breast, prostate, cervical, ovarian, colon, brain, pancreatic and lung cancers, leukemias and lymphomas, and others mentioned hereinabove. Persons of skill in the art will be able to determine by routine experimentation the types of tumors that are amenable to treatment.

Treatment may be administered alone, or as an adjuvant to surgery, e.g. before surgery, for example, to reduce tumor size, and/or following surgery to reduce the possibility of metastases, e.g. by inhibition of the growth and migration of circulating tumor cells through the blood stream.

The invention also provides a method of prolonging the life of a mammal having a malignant tumor, said method comprising administering to the mammal an effective amount of nordihydroguaiaretic acid (NDGA) or a derivative thereof of formula I:

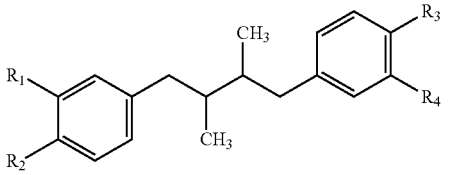

(I)

wherein $R_1$, $R_2$, $R_3$ and $R_4$ independently represent hydroxy, a straight or branched chain lower alkyl or alkoxy, an amino acid residue, a substituted amino acid residue, and a saccharide residue; the amino acid residue, substituted amino acid residue or saccharide residue being optionally joined to the phenyl ring by a linker of an oxygen atom and 1-10 carbon atoms;

and an effective amount of a metabolic modulator.

In one specific embodiment, the NDGA derivative is [tetra-o-methyl] *tetra-O-methyl* nordihydroguaiaretic acid ($M_4N$)[,]. In another specific embodiment, the NDGA derivative is maltose $M_3N$ (90). In other specific embodiments, $R_1$, $R_2$, $R_3$ and $R_4$ are identical and represent straight or branched chain lower alkoxy groups or naturally occurring amino acid residues.

The mammal can be any mammal afflicted with a tumor amenable to treatment, for example a human, nonhuman primate, cat, dog, mouse, etc. The metabolic inhibitor is selected from the group consisting of an inhibitor of the PDK-1/PI3K/AKT pathway, an inhibitor of the PKCδ/topoisomerase IIα pathway, an inhibitor of mitochondrial permeability transition, and an inhibitor of the mitogen-activated protein kinase (MAPK/RAS) pathway. For example, the metabolic inhibitor is selected from the group consisting of Ly294002, etoposide, Rottlerin, dichloroacetate, cetuximab, trastuzumab, bevacizumab and rapamycin. Etoposide, rapamycin, and water soluble derivatives thereof are expected to be particularly effective.

The tumor may be a solid or hematological tumor, such as, for example, breast, prostate, cervical, ovarian, colon, brain, pancreatic and lung cancers, leukemias and lymphomas, and other tumors mentioned hereinabove. Persons of skill in the art will be able to determine by routine experimentation the types of tumors that are amenable to treatment.

Formulations and Administration Suitable for IV, IP, Topical and Oral Application.

Pharmaceutical compositions in accordance with the invention, are useful for diagnosis, prognosis, prophylaxis or treatment of a condition. Accordingly, compositions in accordance with the invention are useful as a drug or as information for structural modification of existing compounds, e.g., by rational drug design. Compounds and methods of the invention are useful for screening compounds having an effect on a variety of conditions.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the drug in the patient. Treatment of human patients or other animals are generally carried out using a therapeutically effective amount of a therapeutic of the invention in a physiologically-acceptable carrier. Suitable carriers and their formulation are described, for example, in Remington's Pharmaceutical Sciences by E. W. Martin.

The amount of the therapeutic agent to be administered varies depending upon the manner of administration, the age and body weight of the subject/patient, and with the subject's symptoms and condition. A compound is administered at a dosage that best achieves medical goals with the fewest corresponding side effects.

Administration

The pharmaceutical compositions of this invention including biologically active fragments, variants, or analogs thereof, can be administered by any suitable routes including intracranial, intracerebral, intraventricular, intrathecal, intraspinal, oral, topical, rectal, transdermal, subcutaneous, intravenous, intramuscular, intranasal, and the like. In one embodiment, the compositions are added to a retained physiological fluid, such as cerebrospinal fluid, blood, or synovial fluid. The compositions of the invention can be amenable to direct injection or infusion at a site of disease or injury.

Compositions for parenteral use may be provided in unit dosage forms (e.g., in single-dose ampules), or in vials containing several doses and in which a suitable preservative may be added. The composition may be in the form of a solution, a suspension, an emulsion, an infusion device, or a delivery device for implantation, or it may be presented as a dry-powder to be reconstituted with water or another suitable vehicle before use. The composition may include suitable parenterally acceptable carriers and/or excipients.

In one approach, a therapeutic of the invention is provided within an implant, such as an osmotic pump, or in a graft comprising appropriately transformed cells. Methods of introduction may also be provided by rechargeable or biodegradable devices. Various slow release polymeric devices have been developed and tested for the controlled delivery of drugs, including proteinaeious biopharmaceuticals. A variety of biocompatible polymers (including hydrogels), including both biodegradable and non-degradable polymers, can be used to form an implant for the sustained release of a bioactive factor at a particular target site.

Generally, the amount of administered agent of the invention (dosage) will be empirically determined in accordance with information and protocols known in the art. Typically agents are administered in the range of about 10 μg/kg to 100 mg/kg of the recipient. Other additives may be included, such as stabilizers, bactericides, and anti-fungals. These additives will be present in conventional amounts.

Exemplary dosages to be considered are shown in Table 1.

TABLE 1

Estimation of the amounts of Terameprocol, Etoposide, and Rapamycin to be considered in patient treatment

| | | | $K_m$ factor* | | |
|---|---|---|---|---|---|
| | | A. Terameprocol | | | |
| Mouse | 1 mg/day | 30.3 mg/kg | 3 | 90.3 mg/m$^2$ | |
| Human | 171.5 mg/day | 2.45 mg/kg | 37 | 90.3 mg/m$^2$ | As mouse |
| | 859.6 mg/day | 12.28 mg/kg | 37 | 454.5 mg/m$^2$ | 5x mouse |
| | | B. Etoposide | | | |
| Mouse | 0.4 mg/day | 12.1 mg/kg | 3 | 36.3 mg/m$^2$ | |
| Human | 68.6 mg/day | 0.98 mg/kg | 37 | 36.3 mg/m$^2$ | As mouse |
| | 343 mg/day | 4.9 mg/kg | 37 | 181.5 mg/m$^2$ | 5x mouse |
| | | C. Rapamycin | | | |
| Mouse | 0.375 mg/day | 11.1 mg/kg | 3 | 33.3 mg/m$^2$ | |
| Human | 63 mg/day | 0.9 mg/kg | 37 | 33.3 mg/m$^2$ | As mouse |
| | 315 mg/day | 4.5 mg/kg | 37 | 166.5 mg/m$^2$ | 5x mouse |

Mouse weight: 33 g

Human weight: 70 kg

*Reference: Dose Translation from Animal to Human Studies S. R. Shaw, M. Nihal, and N. Ahmad The FASEB Journal, Vol. 22 p. 659-661, 2007

Columns 2 and 3 of Table 1 show effective dosages administered in mice in experiments as described herein, and administered to humans in clinical trials. Column 4 shows Km factor for conversion to patient treatment dosage. Column 5 gives the calculated amount for administration to patients. In general it is expected that blood levels of 0.5 to 10 mM of $M_4N$, preferably 1-5 mM, should be achieved for effective patient treatment. Persons of skill in the art will appreciate that the dosage is expected to vary depending on the protocol used for drug administration.

The administration of a compound of the invention may be by any suitable means that results in a concentration of the therapeutic that, combined with other components, is effective in ameliorating, reducing, or stabilizing a deficit or disorder. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Formulation of Pharmaceutical Compositions

As noted above, compositions of the invention can be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, cited herein.

For example, pharmaceutical compositions according to the invention may be in the form suitable for sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanedioi, Ringer's solution, and isotonic sodium chloride solution and dextrose solution. The aqueous formulation may also contain one or more preservatives (e.g., methyl, ethyl or n-propyl p-hydroxybenzoate).

Suitable dosage forms can be formulated for, but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for injection or intravenous administration.

To prepare such pharmaceutical dosage forms, one or more of the aforementioned compounds are intimately admixed with a pharmaceutical carrier according to conventional pharmaceutical compounding techniques. The carrier may take a wide variety of forms depending on the form of preparation desired for administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Methods in accordance with the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

Formulations for oral use include tablets containing active ingredient(s) of the invention in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

As appropriate, a tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

As appropriate, a syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g. intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of the invention may further include one or more accessory ingredient(s) selected from diluents, buffers, flavoring agents, binders, disintegrates, surface active agents, thickeners, lubricants, preservatives (including antioxidants), and the like.

A formulation of the present invention can have immediate release, sustained release, delayed-onset release or any other release profile known to one skilled in the art.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain the enzyme activity at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The compositions of the invention can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the active drug may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Salts and Derivatives

Compositions of the invention can comprise various pharmaceutically acceptable salts, ether derivatives, ester derivatives, acid derivatives, and aqueous solubility altering derivatives of the active compound. The present invention can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

Prodrugs and active metabolites of compounds of the invention are also within the scope of the invention.

A prodrug is a pharmacologically inactive compound that is converted into a pharmacologically active agent by a metabolic transformation. In vivo, a prodrug is acted on by naturally occurring enzyme(s) resulting in liberation of the pharmacologically active agent. Conventional procedures for the selection and preparation of suitable prodrug derivatives are described, for example, in "Design of Prodrugs", ed. H. Bundgaard, Elsevier, 1985.

An active metabolite is a compound which results from metabolism of another compound after administration of the latter to a subject. Metabolites can be identified by techniques well-known in the art.

The invention also comprises kits, e.g., for the treatment, diagnosis, prophylaxis or prognosis of disease or injury. In one embodiment, the kit includes a composition of the invention containing an effective amount of a compound of the invention in unit dosage form. In some embodiments, the kit comprises an outer container or package. The kit can comprise a sterile container which contains a therapeutic; such sterile containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain kit embodiments, a composition of the invention is provided together with instructions for administering it to a subject. Instructions may include information about the use and effects of the composition. In one embodiment, the instructions will include at least one of the following: description of a composition of the invention, dosage schedule and administration protocols, precautions, warnings, indications, counter-indications, overdosage information, adverse reactions, animal pharmacology, clinical studies, and/or references.

The instructions may be printed directly on a container (when present), or as a label applied to the container, or as a separate sheet, pamphlet, card, or folder supplied in, on or with the container. Thus, the instructions may be a separate item in the kit, or be imprinted embossed, molded or otherwise affixed to another item in the kit; instructions may be printed on an outer container and also included as an insert item in the kit.

The effect of $M_4N$ was studied for 4T1 and 67NR cell lines. These cell lines are derived from subpopulations of a single mouse breast cancer although 4T1 is far more metastatic than 67NR cells.

$M_4N$ induced TUNEL-positive cell death more efficiently in 67NR than in 4T1 cells. $M_4N$ suppressed phosphorylation of several PDK-1/PI3K/AKT pathway-related proteins in 67NR but not in 4T1 cells.

We found that manipulations of PDK-1/PI3K/AKT pathway by other drugs could modulate the effect of $M_4N$ on 4T1 cells. Both Ly294002 (phosphatidyl inositol 3-kinase inhibitor) and rottlerin (an inhibitor with broad specificity), were found to promote cell death synergistically with $M_4N$ in both 4T1 and 67NR cells in tissue cultures, Treatment of 4T1 or 67NR tumor-bearing Balb/c female mice with $M_4N$ did not extend the life-span of these mice. However, combination treatment of $M_4N$ with rottlerin extends the life-span of these mice. Additionally combination treatment of $M_4N$ with rottlerin reduced lung metastasis of 4T1 cells, measured by the clonogenicity assay. The data indicates possible clinical applications of combination treatment of $M_4N$ with rottlerin and Ly294002 for cancer therapy.

The effect of five metabolic modulators (Rottlerin, Ly294002, Etoposide, Dichloroaeetate and rapamycin) on induction of rapid cell death by tetra-O-methyl nordihydroguaiaretic acid ($M_4N$, EM1421, Terameprocol) was studied in 4T1 and 67NR mouse breast cancer cell lines and LNCaP human prostate cancer cell line. $M_4N$ induced rapid TUNEL-positive cell death synergistically with either Rottlerin or Ly294002 in 4T1 and 67NR cell lines and with Rottlerin, Ly294002, Etoposide, or Dichloroacetate in LNCaP cells.

$M_4N$, Rottlerin, Ly294002, and Desferoxamine synergistically increased the translocation of phosphor-PKCδ ($Thr^{505}$) into the nuclei. Transfeetion of PKCδ vectors enhanced cell death induced by $M_4N$ in both 4T1 and 67NR cells. On the other hand, transfection with dominant negative PKCδ (kinase negative) vectors partially suppressed cell death induced by a combination treatment of $M_4N$ with either Rottlerin or Ly294002. Rottlerin but not Ly294002 depolarized mitochondrial membrane potential.

The combination treatment of $M_4N$ with Ly294002 markedly suppressed tumor growth and metastasis in nude mice which had been orthotopically implanted with LNCaP tumors. By relieving tumor burdens, the drug combination has so far protected 100% of treated mice from death beyond 112 days while control mice all died before 52 days after tumor transplantation.

Thus, chemicals which affect a very diverse range of cellular metabolisms that are often modulated specifically in cancer cells, such as the phosphatidyl inositol 3-kinase/Akt pathway (Ly294002), PKCδ/topoisomerase IIα pathway (Ly294002, Etoposide, Rottlerin), or mitochondrial permeability transition (Rottlerin, Dichloroacetate) have the ability synergistically to enhance the tumoricidal effect of $M_4N$ on aggressive mouse and human cancers.

$M_4N$ was evaluated in a mammary tumors at two different stages metastatic (cell line 4T1) and nonmetastatic (cell line 67NR). $M_4N$ is effective to stop the growth of metastatic 4T1 cells but not sufficient to induce cell apoptosis within first 48 hours, although it is able to induce apoptosis in nonmetastatic 67NR cells, (20).

A particularly compelling observation was that $M_4N$ together with low amounts of additional drugs (drugs that may be correlated with toxicity at higher does) is both efficacious and had essentially nontoxic side effects. In one method of the invention, $M_4N$ or another NDGA derivative is administered daily with a metabolic inhibitor until an effective dosage is achieved in plasma and in the target cells to have the desired therapeutic effect without the toxicity associated with higher dosages that are necessary when only one drug is administered.

Other features and advantages of the invention will be apparent from the detailed description, and from the claims.

DEFINITIONS

By "agent" is meant a polypeptide, peptide, nucleic acid molecule, small molecule, or mimetic.

By "analog" is meant an agent having structural or functional homology to a reference agent.

By "cell substrate" is meant the cellular or acellular material (e.g., extracellular matrix, polypeptides, peptides, or other molecular components) that is in contact with the cell.

By "control" is meant a standard or reference condition.

By "disease" is meant any condition or disorder that damages or interferes with the normal function of a cell, tissue, organ or subject.

By "effective amount" is meant the amount of an agent required to ameliorate the symptoms of a disease relative to an untreated patient. The effective amount of an active therapeutic agent used to practice the present invention for the treatment of a disease or injury varies depending upon the manner of administration, the age, body weight, and general health of the subject. Ultimately, the attending clinician will decide the appropriate amount and dosage regimen.

By "fragment" is meant a portion of a polypeptide that has at least 50% of the biological activity of the polypeptide from which it is derived. This portion contains, preferably, at least 10%, 20%, 30%, 40%, 50%, 60%, 70%, 80%, or 90% of the entire length of the reference nucleic acid molecule or polypeptide, A fragment of a polypeptide or nucleic acid molecule may contain 10, 20, 30, 40, 50, 60, 70, 80, 90, or 100, 200, 300, 400, 500, 600, 700, 800, 900, or 1000 nucleotides or amino acids.

"HIF" refers to hypoxia inducible factor-1

"$M_4N$" refers to Tetra-O-methyl nordihyroguaiaretic acid, EM 1421 or Terameprocol, each of which are synonyms.

"Lower alkyl" and "lower alkoxy" refer to alkyl and alkoxy groups of 1-6 carbon atoms.

By "modifies" is meant alters. In the context of the invention, an agent that modifies a cell, substrate, or cellular environment produces a biochemical alteration in a component (e.g., polypeptide, nucleotide, or molecular component) of the cell, substrate, or cellular environment.

"MTT" refers to 3-(4,5-Dimethylthiazol-2-yl)-2,5-diphenyltetrazolium bromide.

"PDK-1" indicates 3'-phosphoinositide-dependent protein kinase-1.

"PI3K" refers to phosphatidyl inositol-3-kinase

"mTOR" refers to the mammalian target of rapamycin.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, a "prodrug" is a pharmacologically inactive compound that is converted into a pharmacologically active agent by a metabolic transformation.

By "subject" is meant a mammal, including, but not limited to, a human or non-human mammal, such as a bovine, equine, canine, ovine, or feline.

By "therapeutic delivery device" is meant any device that provides for the release of a therapeutic agent. Exemplary therapeutic delivery devices include osmotic pumps, indwelling catheters, and sustained-release biomaterials.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "variant" is meant an agent having structural homology to a reference agent but varying from the reference in its biological activity. Variants provided by the invention include optimized amino acid and nucleic acid sequences that are selected using the methods described herein as having one or more desirable characteristics.

As used herein, "inhibiting" means slowing or stopping the growth of.

As used herein, "with" or "along with" means that the compounds are administered during the same course of treatment, but not necessarily simultaneously. Administration may occur seconds, minutes, or hours apart in time, but will preferably be closely spaced (at least minutes). The compounds should be administered for sufficient duration (e.g. daily) so that an effective dosage is achieved in plasma and in the target tumor cells.

At 18 days after inoculation, the tumors were excised from the mice and their weights were measured. Data are presented as means (+/−) SD. The difference between the control and the combination treatment is statistically significant by Student's t-test (2%). C: At 18 days after inoculation, the lungs were excised from the mice and the clonogenicity assay was performed. Data are presented as means (+/−) SD. The difference between the control and the combination treatment is statistically significant by Student's t-test (2%).

Figure 8:
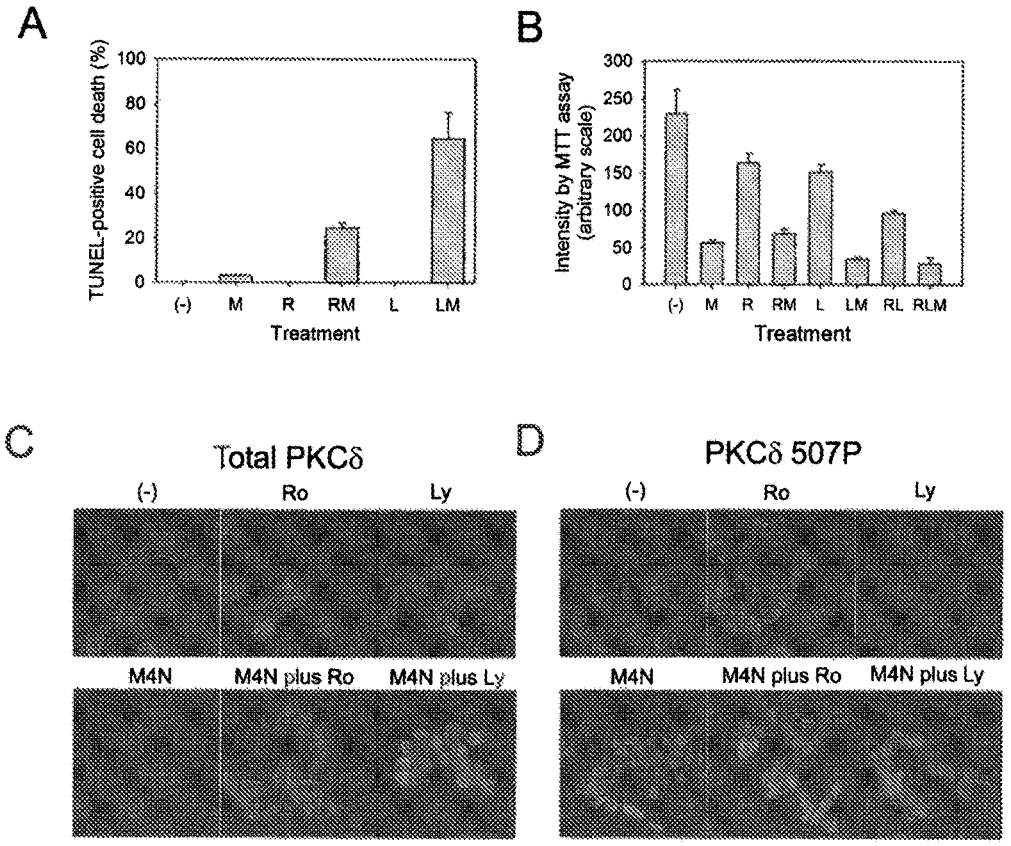

FIG. 8. Effect of $M_4N$, Rottlerin, and Ly294002 on TUNEL-positive cell death (A), cell growth (B), and cellular localization of total PKCδ (C) & phosphor-PKCδ ($Thr^{507}$) (D) in LNCaP cells. The concentration of $M_4N$ (M), Rottlerin (R), and Ly294002 (L), is 80 μM, 5 μM, and 20 μM respectively. Cell death was measured at 28 hrs after treatment (A), Cell growth assayed by the MTT method was measured at 24 hrs after treatment (B). Data are presented as means (+/−) SD in triplicates (A & B). The cellular localization of PKCδ (C) and phosphor-PKCδ ($Thr^{507}$) (D) was examined at 5 hrs after treatment.

Figure 9:
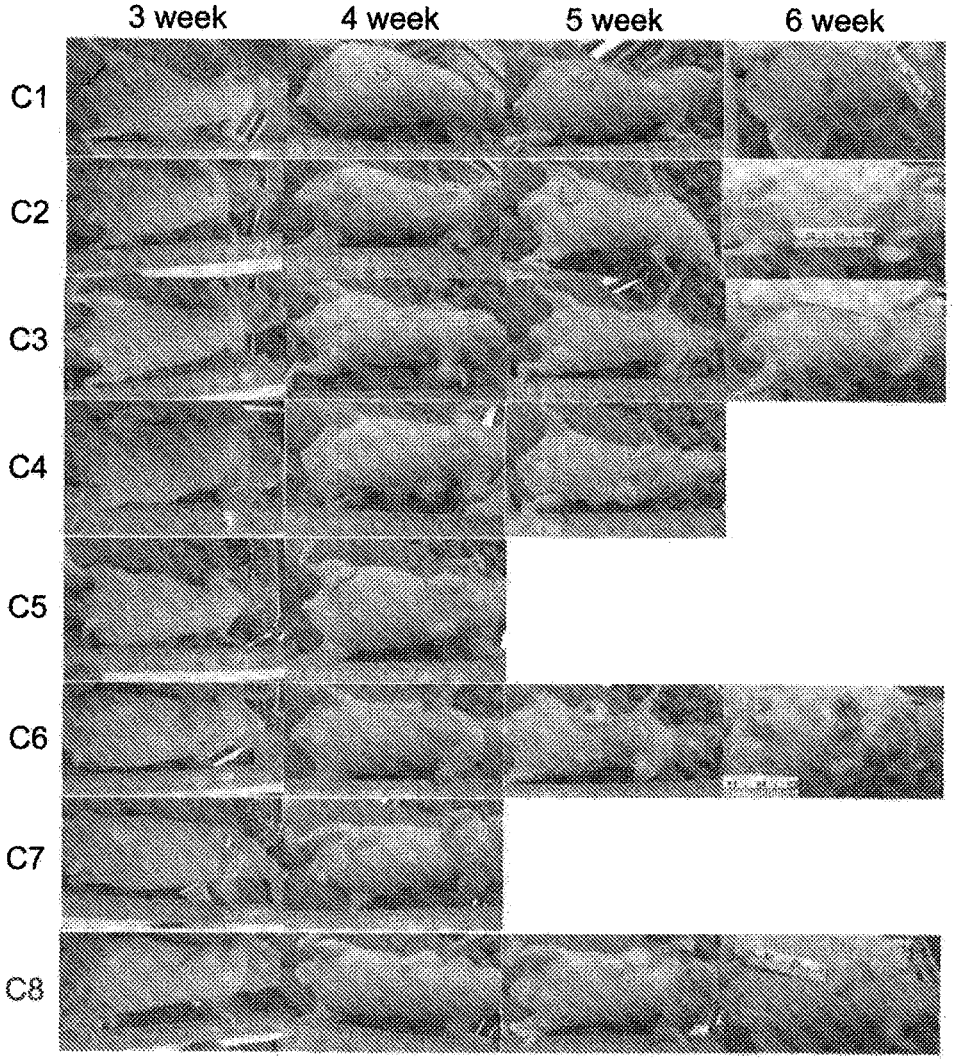

FIG. 9. Metastatic tumors which appeared on the ventral side of nude (nu/nu) mice orthotropically implanted with LNCaP tumors without treatment. There are eight mice with arbitrary designations on the right side of the panels. The pictures were taken after 3 to 6 weeks after inoculation of tumors. The mice were daily injected with vehicle only. Vehicle injections started 8 days after implantation of tumors. Metastatic tumors are circled by red dots in the pictures.

Figure 10:
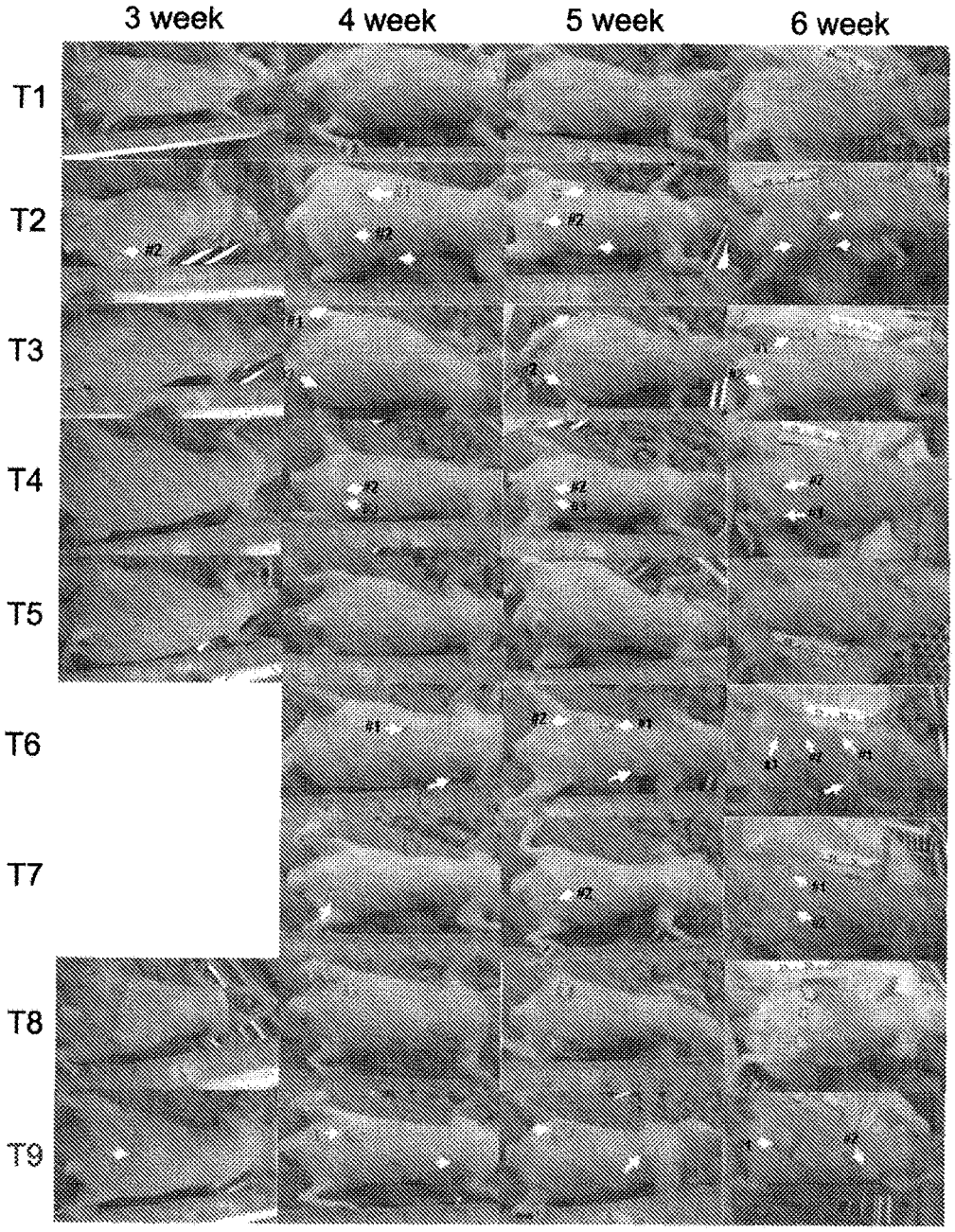

FIG. 10. Metastatic tumors which appeared on the ventral side of nude (nu/nu) mice orthotropically implanted with LNCaP tumors with a combination treatment of $M_4N$ with Ly294002. There are eight mice with arbitrary designations on the right side of the panels. The pictures were taken after 3 to 6 weeks after inoculation of tumors. The mice were daily injected with $M_4N$ (1 mg/shot) and Ly294002 (100 μg/shot). Drug injections started 8 days after implantation of tumors. Metastatic tumors are circled by red dots in the pictures.

Figure 11:
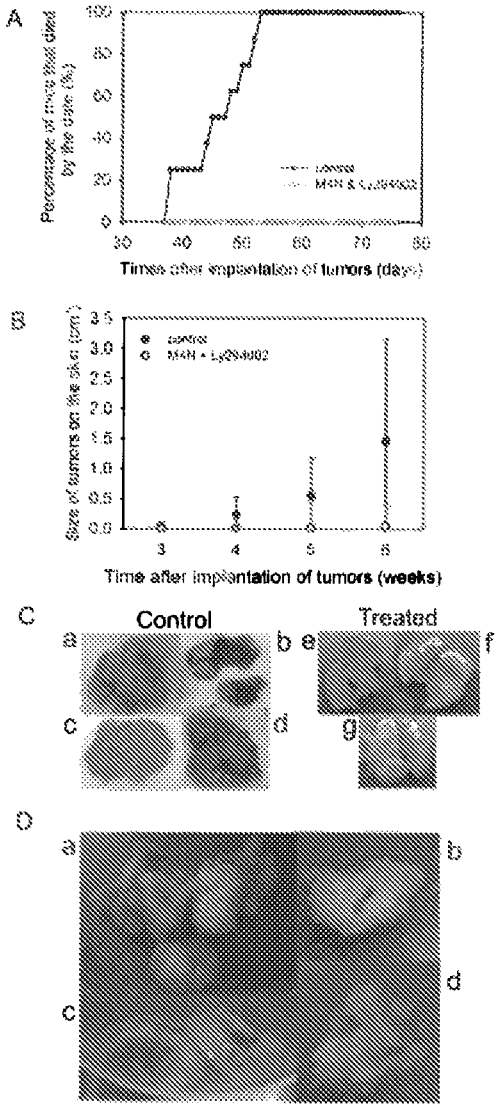

FIG. 11, Effect of combination treatment of $M_4N$ and Ly294002 on nude (nu/nu) mice orthotropically implanted with LNCaP tumors. LNCaP tumors were orthotropically implanted into the vicinity of prostate glands in male nude mice. Effect of combination treatment of $M_4N$ (1 mg/shot) and Ly294002 (100 μg/shot) was examined. Drug injections started 8 days after implantation of tumors. Drugs were administered 7 days a week. A: The percentage of mice that have died by the date after tumor inoculation was shown for each group. B: Many tumor lesions appeared on the body surface of tumor-bearing mice in one to two weeks after tumor implantation. The size of these tumor lesions was estimated by the calculation described in Materials & Methods. Data are presented as means (+/−) SD. The difference between the control and the combination treatment at both 5 and 6 weeks after tumor implantation is statistically significant by Student's t-test (5%). C: The lungs (a & b) and the internal thoracic region facing the lungs (c & d) from the control mice that died of cancer at 7 to 8 weeks after tumor implantation. The lungs (e-g) from the treated mice that were killed at 11 weeks after tumor implantation. D: The tumors from the treated mice that were killed at 11 weeks after tumor transplantation. The tumors were cut by the scalpel so that their inside could be seen, a: the tumor in the prostate region, b-d: the tumors in the abdominal skin.

Figure 12:
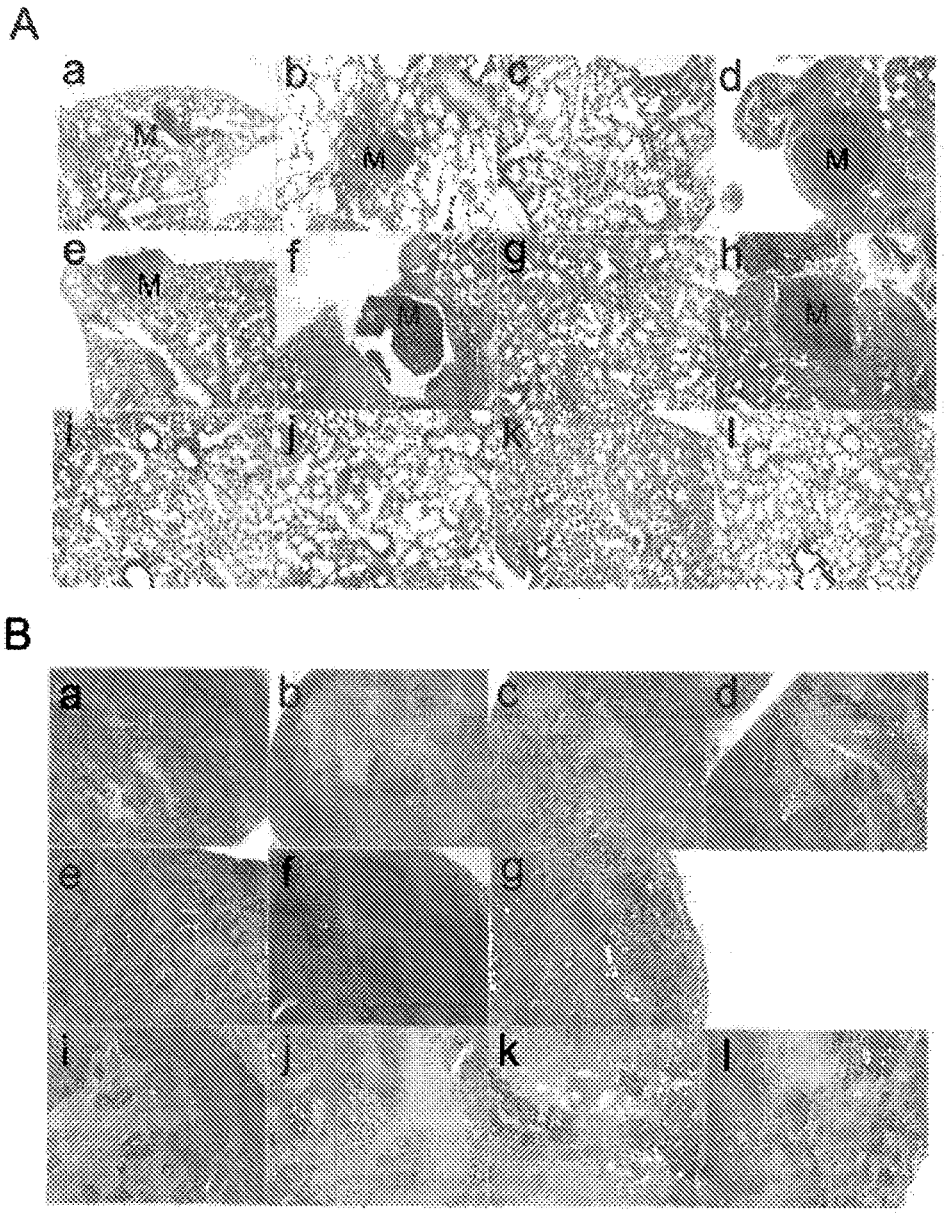

FIG. 12. Effect of combination treatment of $M_4N$ and Ly294092 on metastatis tumors in the lung and the skin in nude (nu/nu) mice orthotropically implanted with LNCaP tumors. A: Histological images of the lungs from eight different control mice that died of cancer at 7 to 8 weeks after tumor implantation (a-h). Metastasis lesions (designated as 'M') exist in six out of eight those mice. Notice that there is not any obvious metastasis lesion in the lung from all four different treated mice that were killed at 11 weeks after tumor implantation (i-l). B; Many tumor lesions appeared on the body surface of tumor-bearing mice in one to two weeks after tumor implantation. Histological images of these lesions from either seven different control mice that died of cancer at 7 to 8 weeks after tumor implantation (a-g) or four different treated mice that were killed at 11 weeks after tumor implantation (i-l). All the sections were stained with Hematoxylin and Eosin.

Figure 13:
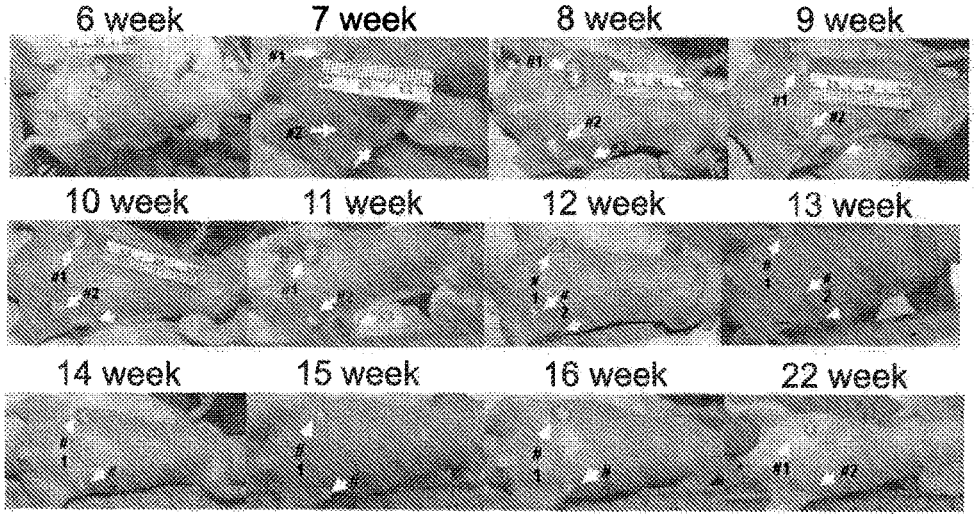
Figure 13:
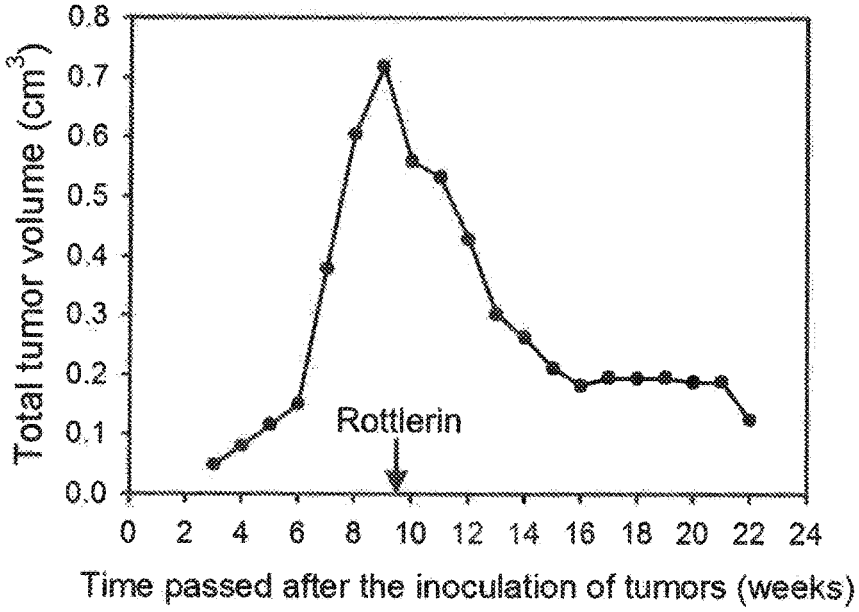

FIG. 13. Effect of additional Rottlerin treatment on metastatic tumors which appeared on the ventral side of T8 mouse orthotropically inoculated with LNCaP cells and treated with $M_4N$ and Ly294002. A: Images of metastatic tumors on the ventral side of T8 mouse from 6 to 22 weeks after inoculation of tumors. B: Total volumes of metastatic ventral tumors in T8 mouse from 3 to 22 weeks after inoculation of tumors. T8 mouse in this figure is the same one as T8 mouse in FIG. 3. The mice was daily treated with $M_4N$ (1 mg/shot) and Ly294002 (100 μg/shot). Drug injections started 8 days after implantation of tumors. Rottlerin (100 μg/shot) was additionally administered to the mice 10 weeks after the tumor inoculation.

Figure 14:
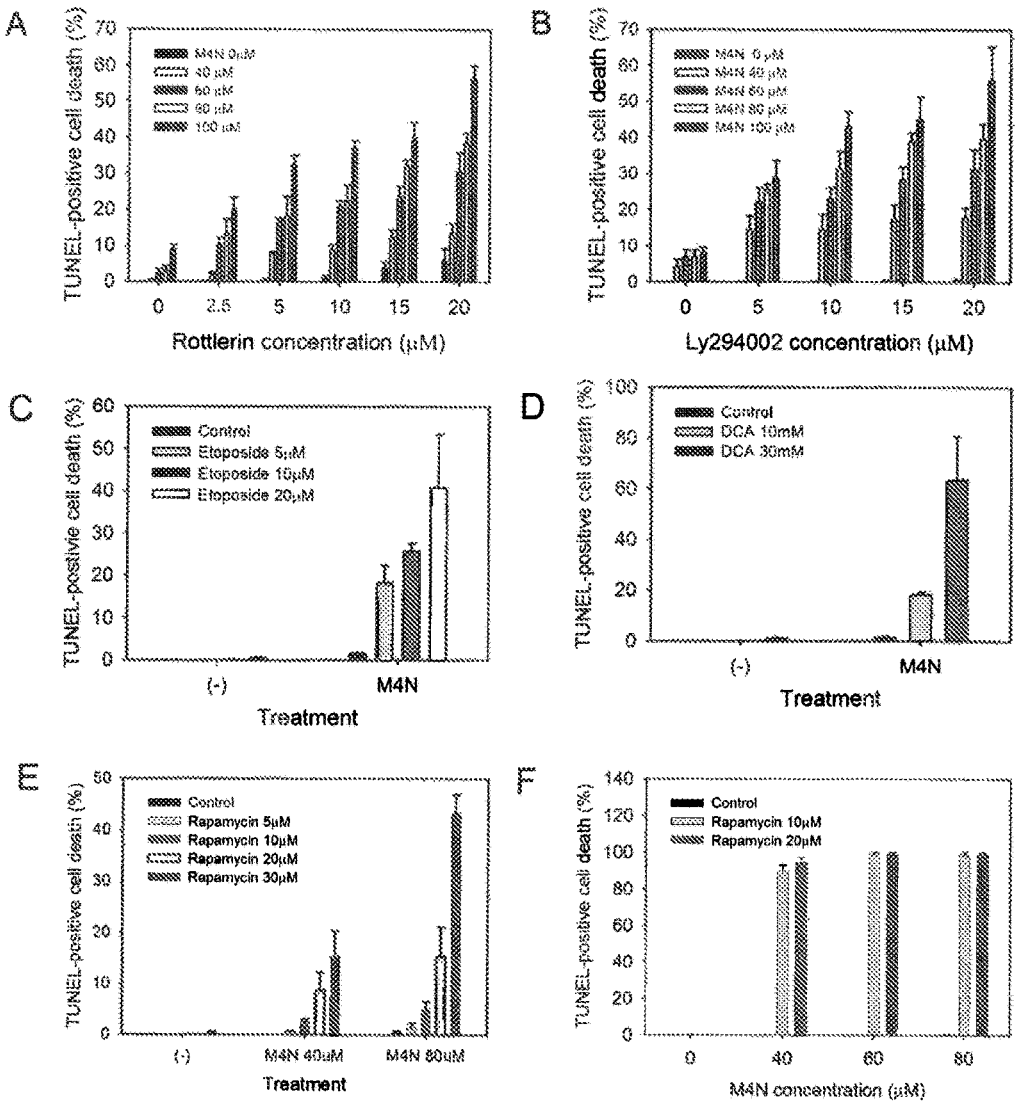

FIG. 14. A & B: Effect of the combination treatment of $M_4N$ with different metabolic modulators on TUNEL-positive cell death in LNCaP cells with different concentrations of drugs 24 hrs or 48 hrs after treatment. LNCaP cells were treated with $M_4N$ in the combination with either Rottlerin (A) or Ly294002 (B). Etoposide (C), Dichloroacetate (D), or Rapamycin (E&F) at either 24 hrs (C, D & E) or 48 hrs (F). $M_4N$ (40 μM, 60 μM or 80 μM), Etoposide (5, 10, or 20 μM), Dichloroacetate (10 or 30 mM) or Rapamycin (5, 10, 20, or 30 μM) were used. Data are presented as means (+/−) SD in triplicates (A-F).

Figure 15:
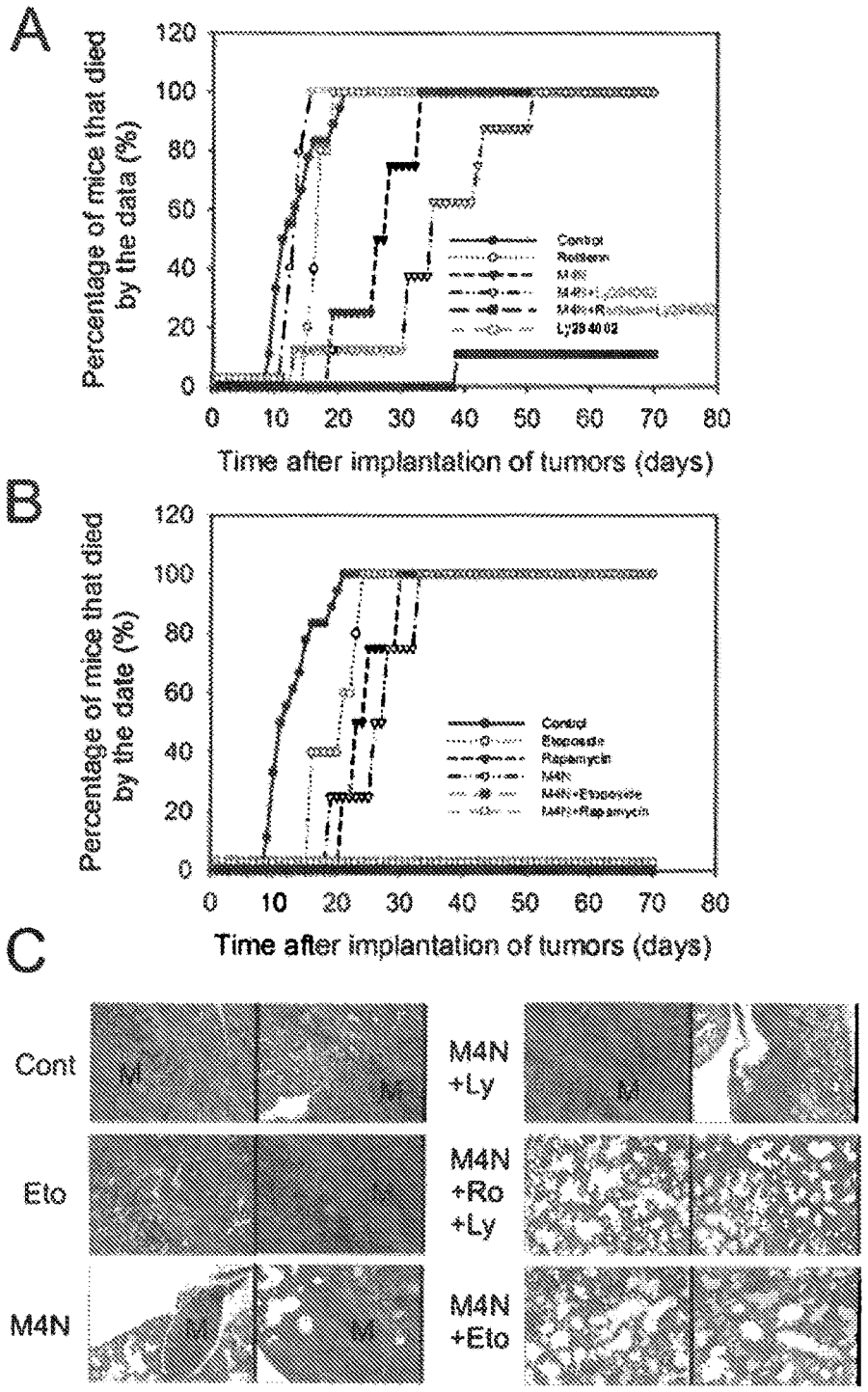

FIG. 15. Effect of combination treatment of $M_4N$ with either Ly294002, Rottlerin plus Ly294002 or etoposide on nude (nu/nu) mice orthotropically implanted with LNCaP tumors. LNCaP tumors were orthotropically implanted into the vicinity of prostate glands in male nude mice. A; Effect of the combination treatment of $M_4N$ with either Ly294002 or Rottlerin plus Ly294002 on the life-span of tumor-bearing mice. The percentage of mice that have died by the date after tumor inoculation was shown for each group. The numbers of mice in each group were 18, 5, 4, 8, and 9 for the control, Rottlerin alone, $M_4N$ alone, $M_4N$ & Ly294002, and $M_4N$ & Rottlerin & Ly294002 group respectively. Dosages of each injection were 1 mg/shot (for $M_4N$), 0.2 mg/shot (for Ly294002), and 0.1 mg/shot (for Rottlerin). Drug injections started 3 days after implantation of tumors. Drugs were administered 7 days a week for four weeks. After that drugs were injected once a week. B: Effect of the combination treatment of $M_4N$ with either Etoposide or Rapamycin on the life-span of tumor-bearing mice. The percentage of mice that have died by the date after tumor inoculation was shown for each group. The numbers of mice in each group were 18, 5, 4, 4, 9 and 5 for the control, Etopside alone, Ly294002 alone, Rapamycin alone, $M_4N$ alone, $M_4N$ & Etoposide, and $M_4N$ & Rapamycin group respectively. Dosages of each injection were 1 mg/shot (for $M_4N$), 0.4 mg/shot (for Etoposide), and 0.375 mg/shot (for Rapamycin). Drug injections started 3 days after implantation of tumors. Drugs were administered 7 days a week for four weeks. After that drugs were injected once a week. C: Histological images of the lung from the tumor-bearing mice treated with different methods. Hematoxylin and Eosin staining. 100× magnification images. M indicates metastasis lesions, Cont, Eto, $M_4N$, $M_4N$+Ly, $M_4N$+Ro+Ly, and $M_4N$+Eto indicate 'control', 'Etoposide alone', '$M_4N$ alone', '$M_4N$ and Ly294002 combination', '$M_4N$, Rottlerin, and Ly294002 combination', and '$M_4N$ and Etoposide combination'.

Figure 16:
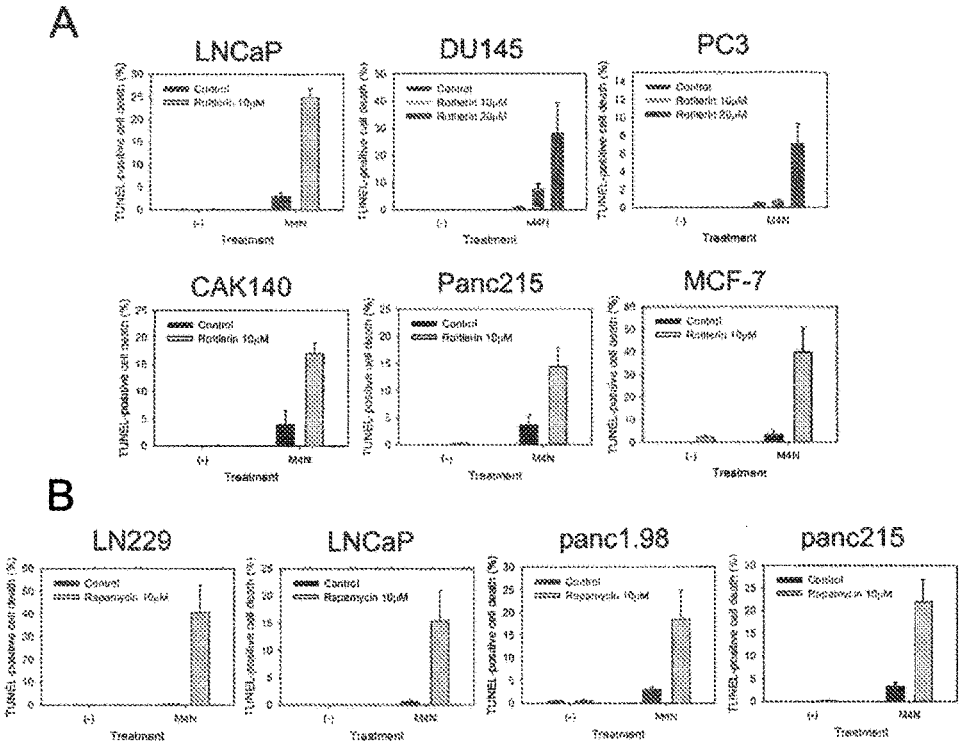

FIG. 16. Effect of combination treatment of $M_4N$ with either Rottlerin or Rapamycin in various tumor cell lines, A: TUNEL-positive cell death in various tumor cell lines treated with $M_4N$ and Rottlerin for 24 hrs. B: TUNEL-positive cell death in various tumor cell lines treated with $M_4N$ and Rapamycin. The concentration of $M_4N$, Rottlerin, and Rapamycin is 80 μM, either 10 or 20 μM, and 10 μM respectively. Data are presented as means (+/−) SD in triplicates.

DETAILED DESCRIPTION AND EXAMPLES

Materials and Methods

Cell Culture Either cell line 4T1 or 67NR was a gift from Dr. Miller (20). The cells were cultured in RPMI1640 medium supplemented with glucose (14 mM), pyruvate (1 mM), penicillin (100 units/ml), streptomycin (100 μg/ml), and fetal bovine serum (10%), buffered with 25 mM HEPES (pH 7.4). LNCaP human prostate cancer cell line was purchased from American Type Culture Collection (Manassas, Va.). The cell line was cultured in RPMI1640 medium supplemented with glucose (14 mM), pyruvate (1 mM), penicillin (100 units/ml), streptomycin (100 μg/ml), and fetal bovine serum (10%). Drugs were dissolved in dimethyl sulfoxide (DMSO) at a suitable concentration so that the final concentration of DMSO in the medium was less than 0.1%.

Reagents: $M_4N$ was synthesized and supplied by Erimos Pharmaceutical, L.L.C. (Raleigh, N.C.), according to the method described (87). Rottlerin was from Calbiochem (San Diego, Calif.). Ly294002 was from Cell Signaling Technology (Danvers, Mass.). zVAD-fmk was from R&D systems (Minneapolis, Minn.). Mouse anti-actin antibodies were from Sigma (Saint Louis, Mo.). Rabbit anti-HIF, anti-caspase 9, anti-phospho-PDK1 ($Ser^{241}$), Akt, phospho-Akt ($Ser^{473}$) (193H12), Phospho-Raf ($Ser^{259}$), and Phospho-MEK1/2 ($Ser^{217/221}$) antibodies were obtained from Cell Signaling Technology (Danvers, Mass.). Rabbit anti-phospho-PRAS40 ($Thr^{246}$) antibody was from Biosource (Camarillo, Calif.). Desferoxamine mesylate and Etoposide were from Sigma (Saint Louis, Mo.). Sodium Dichloroacetate was from Alfa Aesar (Lancashire, UK). Mouse anti-Actin antibody was from Sigma (Saint Louis, Mo.). Rabbit anti-protein kinase Cδ (C-terminal) and anti-phosphor-protein kinase Cδ ($Tyr^{187}$) were from Santa Cruz Biotechnology (Santa Cruz, Calif.). Rabbit anti-caspase 9 and phospho-protein kinase Cδ ($Thr^{505}$) antibodies were obtained from Cell Signaling Technology (Danvers, Mass.).

Animals: Female Balb/e mice were obtained from Charles River Laboratories (Wilmington, Mass.). $M_4N$ and Rottlerin were dissolved into a solvent, CPE (25/30) solvent system supplied by Erimos Pharmaceutical, L.L.C. (Raleigh, N.C.) and injected into mice either intravenously or intraperitoneally, T-cell deficient male nude mice (nu/nu) were obtained from Charles River Laboratories (Wilmington, Mass.). $M_4N$ and Ly294002 were dissolved into a solvent, CPE (25/30) solvent system supplied by Erimos Pharmaceutical, L.L.C. (Raleigh, N.C.) and injected into mice intravenously.

Tumor inoculation: Either 4T1 or 67NR cells were grown as described above. Cells growing subconfluently were collected and resuspended into the tissue culture medium minus fetal bovine serum and antibiotics, After counting the number of the cells, the cell concentration was adjusted. Twenty μl of the solution containing a selected number of cancer cells (either $5\times10^3$ or $5\times10^4$ cells) was injected into each fat pad of a pair of mammary glands located close to lower limbs. Tumor size was measured by weighing tumors extracted from mouse cadavers.

Clonogenicity assay for lung metastasis: Clonogenicity assay was done based on the method by Pulanski & Ostrand-Rosenberg (80). At a selected time following tumor inoculation, mice were euthanized, mouse lungs were removed and minced well. Minced lungs were digested in 1 mg/ml collagenase type IV (Sigma, Saint Louis, Mo.) in phosphate buffered saline without magnesium and calcium (PBS (−)) at 37C for 2 hrs. Digested lungs were filtered through 70 μM cell strainers to remove debris. Cells were washed with PBS (−) and resuspended in the cell culture medium described above, supplemented with 60 μM thioguanine (Sigma, Saint Louis, Mo.). After culturing the cells for several days, the numbers of emerging cell clones were counted.

MTT assay: Cells were incubated in PBS (−) supplemented with 5% fetal calf serum and 0.5 mg/ml MTT, 3-(4,5-Dimethylthiazol-2-yl)-2,5-diphenyltetrazolium bromide (Sigma, Saint Louis, Mo.) for 2 hrs. After the incubation, the cells were dissolved in dimethyl sulfoxide and the color of the solutions was measured by a spectrophotometer at wavelengths of 540 and 690 nm. The values correlated with viable cell numbers were obtained by subtracting the optical density at 690 nm from that, at 540 nm.

Apoptosis assay: Simple TLTNEL assay was conducted by using TUNEL apoptosis detection kit (Upstate, Temecula, Calif.) with some modification. For the evaluation of the effect of PKCδ wild type and dominant negative vectors on TUNEL-positive cell death, we first transfected 4T1 or 67NR cells with these vectors by effectene (Qiagen, Valencia, Calif.). Wild type PKCδ vector is constructed from wild type PKCδ gene and pEGFP (Promega, Madison, Wis.). Dominant negative PKCδ vector is constructed from PKCδ gene mutated at a 376th amino acid residue (threonine) and pEGFP (Promega, Madison, Wis.) This threonine residue is located in ATP-binding domain of protein kinase Cδ, and therefore essential for any kinase reaction of the protein so that this mutant protein supposedly function as dominant negative. As a control we used pEGFP-N3 vector was used. These vectors contain green fluorescent protein (GFP) gene to be used as a transfection marker. The vectors are kind gifts from Dr. Yuspa (National Institutes of Health, Bethesda, Md.) (88). Twenty four hours after transfection, the cells were treated with $M_4N$, Rottlerin, or Ly294002. Then 24 hrs after this treatment with these reagents, the cells were fixed with 10% formaldehyde in phosphate buffered saline without calcium and magnesium (PBS (−)). The cells were then incubated with rabbit anti-GFP antibody (MBL International, Woburn, Mass.) followed by treatment with anti-rabbit IgG antibody conjugated with fluorescein (Promega, Madison, Wis.). TUNEL staining was conducted by using TUNEL apoptosis detection kit (Upstate, Temecula, Calif.) except for using Streptavidin-Alexa Fluor 568 (Molecular Probes, Eugene, Oreg.) instead of Avidine-Rhodamine contained in the kit. Cell death was evaluated by dividing the number of TUNEL-positive cells among the cells positive with anti-GFP staining by the number of these GFP-positive cells.

Western blotting: After cells had been grown in 25 $mm^2$ flasks and treated with reagents, the cells were washed with PBS (−) three times and suspended in RIP A buffer (150 mM NaCl, 50 mM Tris-HCl (pH 8,0), 0.1% SDS, 1% NP40, and 0.5% deoxycholate) supplemented with protease inhibitor cocktail (Calbiochem, San Diego, Calif.). The sample volumes were adjusted by the total protein amount. Protein assay was performed by Bio-Rad Protein Assay (Bio-Rad Laboratories, Inc. Hercules, Calif.). The samples were resolved by the standard SDS-polyacrylamide gel electrophoresis and transferred to nitrocellulose membrane (Amersham Biosciences, Bjorkgatan, Sweden). The membranes were blocked with skim milk, and incubated with primary antibodies at 4° C. overnight and then with secondary antibody conjugated with horse radish peroxidase at room temperature for 2 hrs. The signals were detected by western blot chemiluminescence reagent plus (New England Nuclear Life Science Products, Boston, Mass.).

Surgical orthotropic implantation of LNCaP tumors: LNCaP cells were grown as described above. Cells growing subconfluently were collected and resuspended into the tissue culture medium without fetal bovine serum and antibiotics. After counting the number of the cells, the cell concentration was adjusted using the same medium. After 20 μl of the medium containing a selected number of cancer cells (about $5\times10^7$ cells) had been mixed together with the same volume of Matrigel (BD science, Bedford, Mass.), the combined solution was injected into the skin of nude mice. The tumor tissue growing subcutaneously was used for surgical orthotropic implantation of the tumor into nude mice, according to the method described by Wang et al, (89). The tumor tissue extracted from the skin was excised into pieces of about 2 mm diameter. After nude mice were anesthetized by 2,2,2-Tribromoethanol (Aldrich Chemical Co. Inc., Milwaukee, Wis.), a small incision was made at the abdomen of each mouse and a tumor tissue piece was implanted in the neighbor of the prostate of each mouse. Eight days after the operation, the injection of drugs was initiated, and the drugs were injected intravenously every day for the indicated periods Immunocytocheimstry: Cells were cultured on glass cover slips coated with poly-L-ornithine (Sigma, Saint Louis, Mo.). At 5 hrs after treatment with drugs, the cells were fixed with 10% formaldehyde in diluted in PBS (−) and washed with PBS (−) three times. After permeabilized by 0.2% Tryton X-100 and 1% goat serum diluted in PBS (−), the cells were blocked by PBS (−) containing 5% goat serum. The cells were then incubated with primary antibodies diluted in PBS (−) containing 0.5% bovine serum albumin (BSA), and with secondary antibodies, which is either anti-IgG conjugated with fluorescein (Vector Laboratories. Burlingame, Calif.), diluted in PBS (−) containing 0.5% BSA. The cells were observed through Zeiss fluorescent microscope (Carl Zeiss, Thornwood, N.Y.).

EXAMPLES $M_4N$ has undergone Phase I/II clinical trials in patients by intravenous infusion. Two initial reports of these trials showed that $M_4N$ was able to cause long term stabilization of disease in some patients. However, tumor shrinkage has rarely been seen in patients following $M_4N$ infusion as only limited amount of the drug can be delivered to tumors in situ by the method used.

To increase favorable clinical outcomes, several metabolic modulators have been administered in conjugation with $M_4N$, resulting in rapid induction of tumor apoptosis and reduction of tumor metastases in both mouse breast cancer and human prostate cancer xenograft models.

Example 1

Figure 1:
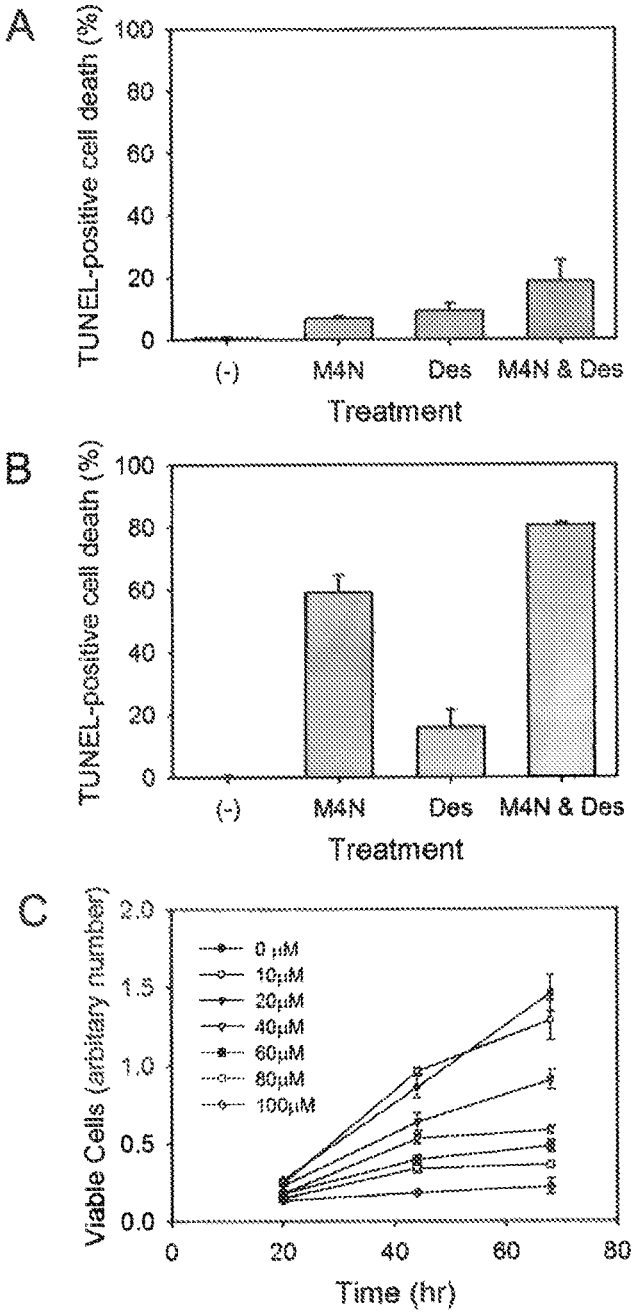
FIG. 1. Effect of $M_4N$ and/or desferoxamine on TUNEL-positive cell death and cell growth in 4T1 and 67NR cells, A and B: Either 4T1 (A) or 67NR. (B) cells at subconfluent condition were treated with $M_4N$ (80 μM) and/or desferoxamine (300 μM). At 48 hrs after treatment the cells were collected and TUNEL assay was performed. C: $1\times10^4$ 4T1 cells were seeded into 12 well plates. One day later, the cells were treated with different concentrations of $M_4N$. The number of cells was measured by MTT assay at different times points. Data are presented as means (+/−) SD in triplicates.

Effect of $M_4N$ to induce cell death in 4T1 and 67NR cells. 4T1 and 67NR cells are the cell lines derived from subpopulations of a mouse breast cancer (20). These two cell lines were characterized by their different behaviors regarding with metastasis. After we had injected either 4T1 or 67NR tumor cells into fat pads of mammary glands of Balb/c female mice, we measured the lung metastasis by the clonogenicity assay (80). At 4 weeks after injections, we did not detect clones in the lungs from 67NR cells while we detected many clones in the lungs from 4T1 cells in all the mice examined (data not shown). The data confirmed that 4T1 cells used in this experiment were more metastatic than 67NR cells, as described earlier (20). Next we examined the effect of $M_4N$, and desferoxamine maleate, a chemical known to mimic hypoxic conditions on cell death, by preventing HIE-1a degradation at Normoxia (21% $O_2$) in 4T1 and 67NR cells (42, 43). We measured cell death by TUNEL assay. At 48 hr after treatment with $M_4N$ we detected more cell death in 67NR cells than 4T1 cells (FIGS. 1A & 1B). Desferoxamine (300 μM) enhanced cell death induced by $M_4N$ in either 4T1 or 67NR cells. Since we did not detect many TUNEL-positive cells in 4T1 cells, we measured the effect of $M_4N$ on cell growth in 4T1 cells by MTT assay (FIG. 1C). MTT assay showed that $M_4N$ reduced the cell growth of 4T1 cells depending on the concentration of the drug. Even at 20 μM of the drug, there was a significant effect of the drug to reduce cell growth. Cell growth stopped at 80 μM, The effect of $M_4N$ on cell growth was evident at 42 hrs after treatment.

Example 2

Figure 2:
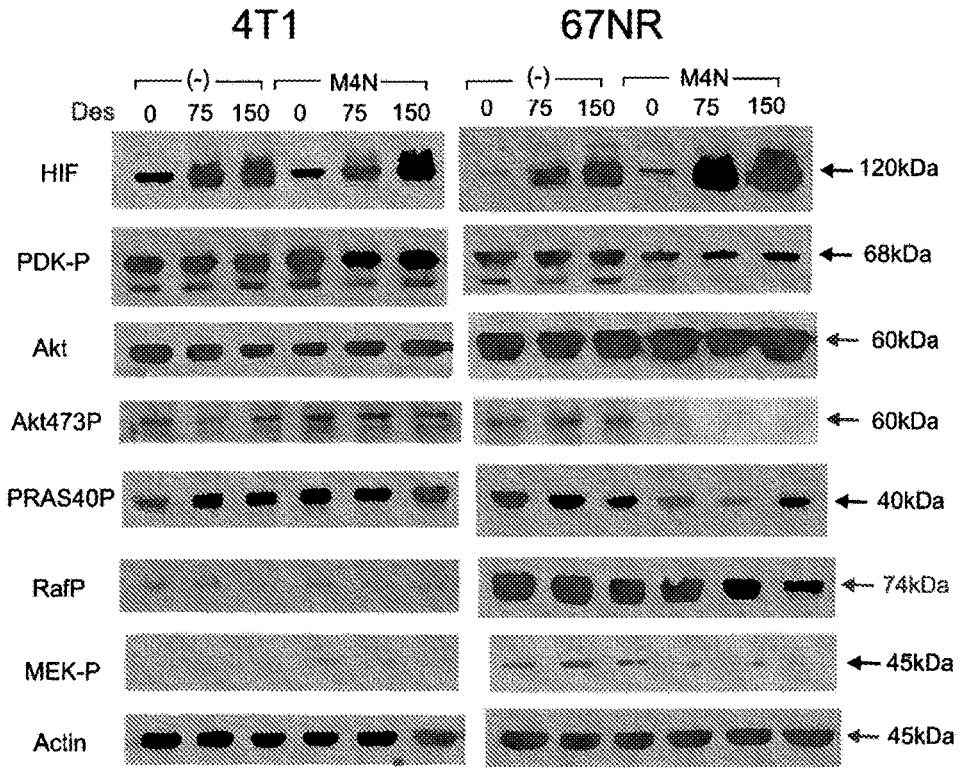
FIG. 2, Effect of $M_4N$ and/or desferoxamine on status of phosphorylated proteins in PDK-1/Akt pathway. Either 4T1 or 67NR cells were seeded into 25 $mm^2$ flasks. One day later, the cells were treated with $M_4N$ (80 μM) and/or Desferoxamine (75 or 150 μM). Five hours later the cells were collected and the western blotting was performed for 4T1 cells and 67NR cells, 0: without desferoxamine, 75: 75 μM desferoxamine, 150: 150 μM desferoxamine, (−): without $M_4N$, and $M_4N$: $M_4N$ (80 μM). PDK-P: phospho-PDK1 ($Ser^{241}$), Akt473P: phospho-Akt ($Ser^{473}$), PRAS40P: phospho-PRAS40 ($Thr^{246}$), RafP; phospho-Raf ($Ser^{259}$), and MEK-P: phospho-MEK1/2 ($Ser^{217/221}$).

Effect of $M_4N$ on phosphorylation status of PDK-1/Akt pathway-related proteins in 4T1 and 67NR cells. Since we found differences between 4T1 and 67NR cells not only in metastasis capability but also susceptibility to $M_4N$ treatment, we next examined the effect of $M_4N$ and desferoxamine on the phosphorylation status of PDK-1/Akt kinase-related proteins of this pathway, which are known to be involved in cell growth and survival (44-47). Strikingly, we found that there were much less phosphorylated Raf and MEK-P detected in $4T_1$ cells compared to that in 67 NR (FIG. 2). In addition, we found that at 5 hrs after treatment there was not much effect in 4T1 cells by either $M_4N$ or desferoxamine on the expression of phosphorylated PDK ($Ser^{241}$), phosphorylated Akt ($Ser^{473}$), phosphorylated PRAS40 ($Thr^{246}$), phosphorylated Raf ($Ser^{259}$), and phosphorylated MEK ($Ser^{217/221}$) (FIG. 2). On the contrary, at 5 hrs after treatment with $M_4N$ in 67NR cells there was significant reduction in the expression of phosphorylated PDK ($Ser^{241}$), phosphorylated Akt ($Ser^{473}$), phosphorylated PRAS40 ($Thr^{246}$), phosphorylated Raf($Ser^{259}$), and phosphorylated MEK ($Ser^{217/221}$) (FIG. 2). PRAS40 (81, 82), Raf (83), and MEK (84) are all downstream phosphorylation targets of Akt. Total Akt expression was not changed much by $M_4N$ in either 4T1 or 67NR cells at 5 hrs after treatment (FIG. 2). Desferoxamine induced HIF stabilization in both 4T1 and 67NR cells, as expected and desferoxamine at 150 μM, a sensor of hypoxic condition, protects HIF very efficiently in both 4T1 and 67NR cells (39). Desferoxamine-mediated HIF induction was slightly suppressed by $M_4N$ in 4T1 cells while it was instead enhanced by $M_4N$ in 67NR cells (FIG. 2). Overall the data indicates that $M_4N$ suppressed PDK-1/Akt-related protein phosphorylation in 67NR cells while it failed to modulate it in 4T1 cells.

Example 3

Figure 3:
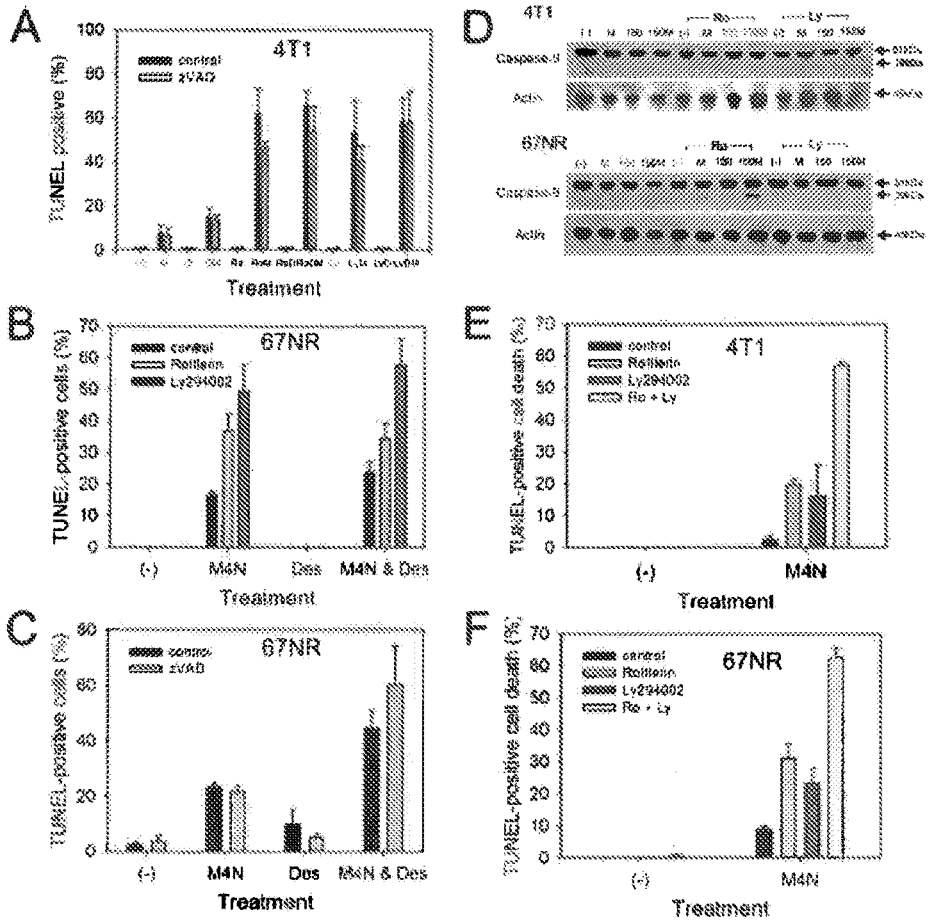
FIG. 3, Effect of $M_4N$, Desferoxamine, Rottlerin, Ly294002, and zVAD on TUNEL-positive cell death in 4T1 and 67NR cells. A: Effect of $M_4N$, Desferoxamine, Rottlerin, Ly294002, and zVAD on TUNEL-positive cell death in 4T1 cells. 4T1 cells at subcontinent condition were treated with $M_4N$ (80 μM), Desferoxamine (150 μM), Rottlerin (5 μM), or Ly294002 (20 μM). At 24 hrs after treatment the cells were collected and TUNEL assay was performed. When the effect of zVAD (50 μM) was examined, zVAD had been added 30 minutes before other drugs were added. M; $M_4N$, D: Desferoxamine, Ro: Rottlerin, Ly: Ly294002. B: Effect of $M_4N$, Desferoxamine, Rottlerin, and Ly294002 on TUNEL-positive cell death in 67NR cells. 67NR cells at subcontinent condition were treated with $M_4N$ (80 μM), Desferoxamine (150 μM), Rottlerin (5 μM), or Ly2940 (20 μM). At 26 hrs after treatment the cells were collected and TUNEL assay was performed. Des: Desferoxamine. C: Effect of zVAD on TUNEL-positive cell death induced by $M_4N$ and Desferoxamine in 67NR cells. 67NR cells at subcontinent condition were treated with zVAD (50 μM), and then treated with $M_4N$ (80 μM) and/or Desferoxamine (150 μM). At 42 hrs later the cells were collected and TUNEL assay was performed. Des: Desferoxamine, A-C: Data are presented as means (+/−) SD in triplicates. D: Effect of $M_4N$, Desferoxamine, Rottlerin, and Ly294002 on caspase-9 cleavage. Either 4T1 or 67NR cells were seeded into 25 $mm^2$ flasks. One day later, the cells were treated with $M_4N$ (80 μM), Desferoxamine (150 μM), Rottlerin (5 μM), and Ly294002 (20 μM), Five hours later the cells were collected and the western blotting was performed for 4T1 cells and 67NR cells. M: $M_4N$, 150: 150 μM Desferoxamine, 150M: $M_4N$ plus 150 μM Desferoxamine, Ro: Rottlerin, Ly: Ly294002. Full length caspase-9 is 51 kDa while cleaved caspase-9 is 39 kDa. E&F: Effect of a combination treatment of three drugs ($M_4N$, Rottlerin, and Ly294002) together on TUNEL-positive cell death in 4T1 (E) and 67NR (F) cells. The concentration of $M_4N$ (M), Rottlerin (Ro), and Ly294002 (Ly) is 80 μM, 5 μM, and 20 μM respectively. The combination treatment of Rottlerin and Ly294002 is indicated by either Ro+Ly or RoLy. Cell death was measured 19 hrs after treatment. Data are presented as means (+/−) SD in triplicates.

Effect of combination treatment of $M_4N$ with PDK-1-related inhibitors, Ro or Ly on cell death in 4T1 and 67NR cells. Since we failed to quickly induce a substantial amount of TUNEL-positive cell death in 4T1 cells, we examined whether a combination treatment of $M_4N$ with other chemicals might be able to induce more cell death in 4T1 cells. For this attempt, we chose Ro and Ly since we observed some difference in the effect of $M_4N$ on PDK-1/Akt-related protein phosphorylation between 4T1 and 67NR cells (FIG. 2). Neither Ro nor Ly alone induced TUNEL-positive cell death in either 4T1 or 67NR cells (FIG. 3). However, a combination treatment of $M_4N$ and Ly induced more cell death than $M_4N$ treatment alone in either 4T1 or 67NR cells (FIGS. 3A & 3B), Meanwhile Ro greatly enhanced cell death induced by $M_4N$ in 4T1 cells while it enhanced to some extent cell death induced by $M_4N$ in 67NR cells as well (FIGS. 3A & 3B). Desferoxamine generally augmented cell death even more. We examined the effect of pan-caspase inhibitor, zVAD, on the TUNEL-positive cell death if this cell death was caspase-dependent. The data showed that zVAD at 50 μM didn't affect TUNEL-positive cell death in either 4T1 or 67NR cells (FIGS. 3A & 3C). Then we examined the caspase-9 cleavage. The data shows that although a small amount of caspase-9 is activated by Ro in 67NR cells and this activation is slightly further augmented by $M_4N$ treatment, caspase-9 activation is overall very weak in either 4T1 or 67NR cells (FIG. 3D). Overall the data suggest that rapid induction of 4T1 and 67NR cells by the combination drug treatment profoundly involves caspase-independent apoptosis mechanisms. We next examined if the combination treatment of $M_4N$ with both Ro and Ly induced more cell death than $M_4N$ with either Ro or Ly alone. The data indicates that Ro and Ly augments $M_4N$-mediated cell death synergistically in 4T1 cells and additively in 67NR cells (FIGS. 3E & 3F). This supports the conclusion that $M_4N$, Ro, and Ly should be useful in combination for anti-cancer treatment.

Example 4

Figure 4:
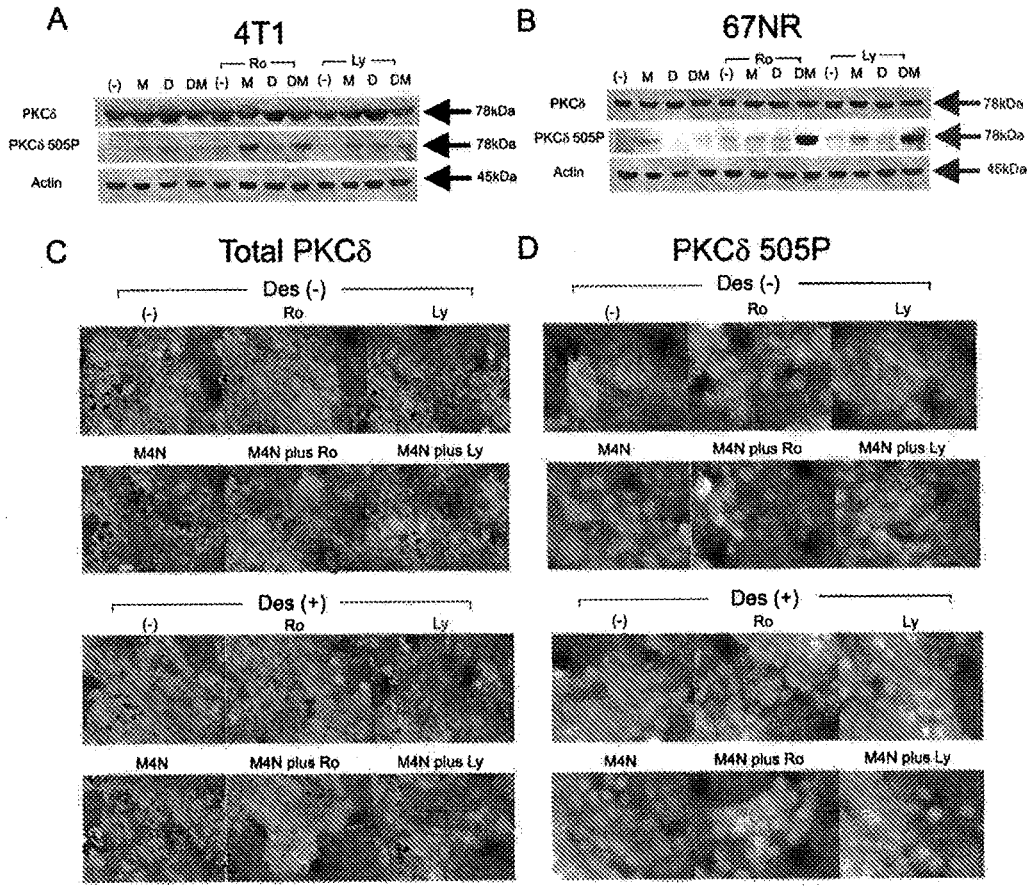
FIG. 4. Effect of $M_4N$, Rottlerin, Ly294002, and Desferoxamine on the expression and cellular localization of total PKCδ and phosphor-PKCδ ($Thr^{505}$) in 4T1 (A) and 67NR cells 5 hrs after treatment. A&B: The expression of the proteins in 4T1 (A) and 67NR (B) detected by the western blotting. The concentration of $M_4N$ (M), Rottlerin (Ro), Ly294002 (Ly), and Desferoxamine (D) is 80 μM, 5 μM, 20 μM, and 150 μM respectively. The combination treatment of Desferoxamine and $M_4N$ is indicated by DM. Actin was used as control. C&D; The cellular localization of total PKCδ (C) and phosphor-PKCδ ($Thr^{505}$) in 4T1 cells. The concentration of $M_4N$, Rottlerin (Ro), Ly294002 (Ly), and Desferoxamine (Des) is 80 μM, 5 μM, 20 μM, and 150 μM respectively. Des (−) indicates 'without Desferoxamine treatment'. Des (+) indicates 'with Desferoxamine treatment'.

Effect of $M_4N$, Ro, Ly, and Des on the expression of total PKCδ and phosphor-PKCδ ($Thr^{505}$) in 4T1 or 67NR cells. PKCδ has been known to be involved in certain types of cell death (27-29). To see if a synergistic induction of $M_4N$-mediated cell death by Ro or Ly occurs through PKCδ, we examined the expression of PKCδ and its phosphorylated form at $Thr^{505}$ residue in 4T1 and 67NR cells at 5 hrs after treatment by the western blotting using phosphor-specific antibodies. Since TUNEL-positive cell death is already very evident in 24 hrs after the combination treatment in this study, we focused on the modifications of PKCδ at 5 hrs after the treatment, assuming that the event which causes cell death need to happen well before the final execution of cell death. Expression of total PKCδ protein was not affected much by the drug treatment alone or in different ways of combinations in both 4T1 cells and in 67NR cells. However the amount of phosphorylated PKCδ at $Thr^{505}$ residue are significantly increased with $M_4N$ plus Ro and $M_4N$ plus Ly combinations in both 4T1 and 67NR cells, especially under conditions mimicking hypoxia through Desferoxamine treatment (FIGS. 4A & 4B).

Example 5

Cellular localization of total PKCδ mid nuclear translocation of phosphor-PKCδ ($Thr^{505}$) in 4T1 cells after treatment with $M_4N$, Ro, Ly, and Des. There were several reports suggesting that translocation of PKCδ into nuclei was required for induction of apoptosis (32, 33). It was also shown that kinase negative full length PKCδ could not be induced to translocate into nuclei by apoptotic stimuli (32), These findings seem to imply that phosphor-PKCδ localized in nuclei might be somehow involved in the mechanism of apoptosis. As shown in FIGS. 4A and 4B, we found that $M_4N$, Ro, Ly, and Des induced phosphorylation of PKCδ at $Thr^{505}$ residue in both 4T1 and 67NR cells. To examine cellular distribution of both total PKCδ and phosphor-PKCδ ($Thr^{505}$), we performed immunohistochemical staining in 4T1 cells after combination treatment of $M_4N$, Ro, Ly, or Des for 5 hrs (FIGS. 4C & 4D). We observed the total PKCδ is distributed more in cytoplasm than nuclei in 4T1 cells (FIG. 4C). $M_4N$, Ro, or Ly treatment alone did not change much the cellular distribution of total PKCδ in the cells. Des did not modulate much nuclear staining of total PKCδ either (FIG. 4C). However, a combination treatment of $M_4N$ with either Ro or Ly in the presence of Des was found to facilitate the accumulation of phosphor-PKCδ ($Thr^{505}$) in the nuclei in 4T1 cells (FIG. 4D).

Example 6

Without any drug treatment, phosphor-PKCδ ($Thr^{505}$) is distributed rather diffusively in 4T1 cells. $M_4N$ treatment augmented staining for phosphor-PKCδ ($Thr^{505}$) in nuclei of the cells (FIG. 4D). Ro also augmented staining for phosphor-PKCδ ($Thr^{505}$) in nuclei. A combination treatment of $M_4N$ with Ro markedly augmented nuclear staining for phosphor-PKCδ ($Thr^{505}$) in a very distinctive manner (FIG. 4D). The nuclear membranous structure was very clearly visible under this condition. Although Ly treatment alone did not significantly modulate the staining in the cells, a combination treatment of $M_4N$ with Ly induced much more nuclear staining than $M_4N$ treatment alone. Des treatment alone only moderately increased nuclear staining in 4T1 cells. However, Des treatment in combination with $M_4N$, $M_4N$ plus Ro, or $M_4N$ plus Ly markedly augmented nuclear staining in the cells (FIG. 4D).

Example 7

Figure 5:
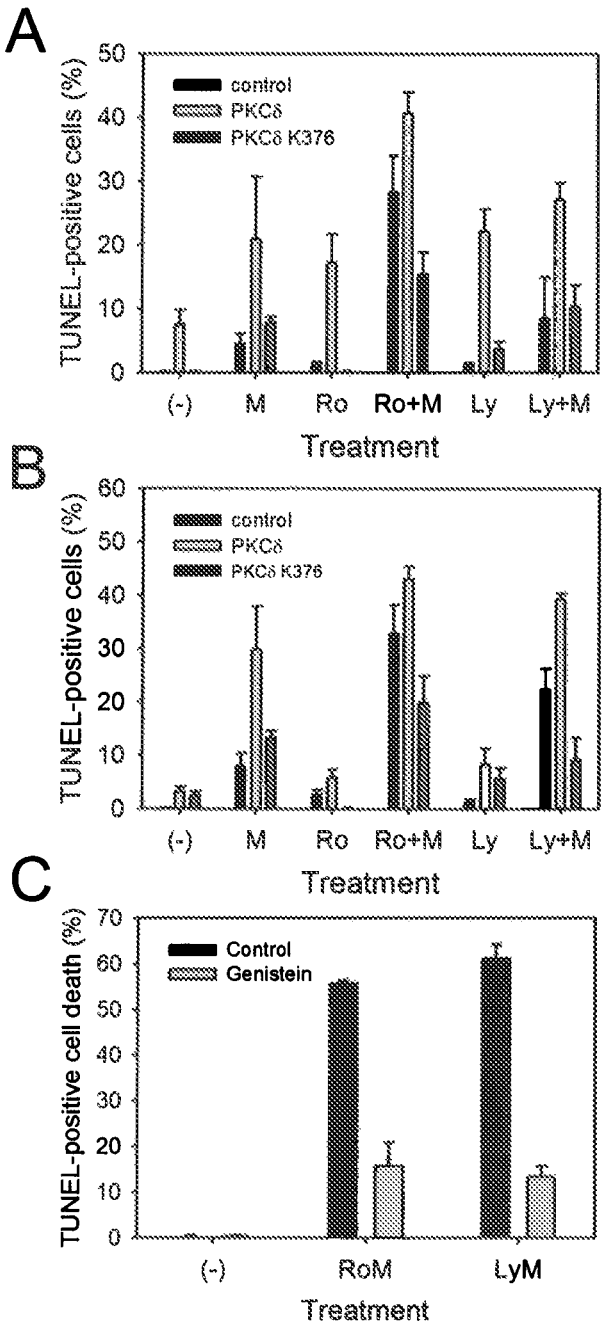
FIG. 5. Effect of PKCδ wild type and K376 mutant PKCδ (kinase negative) type vectors on TUNEL-positive cell death induced by $M_4N$, Rottlerin, and Ly294002 in 4T1 (A) and 67NR (B) cells 24 hrs after treatment. The concentration of $M_4N$ (M), Rottlerin (Ro), Ly294002 (Ly), and Desferoxamine (Des) is 80 μM, 5 μM, 20 μM, and 150 μM respectively. A (4T1 cells): The difference between the control and the PKCδ wild type in cells treated with $M_4N$ is statistically significant by t-test (5%). The difference between the control and the PKCδ wild type in cells treated with $M_4N$ and Rottlerin is statistically significant by t-test (5%). The difference between the control and the PKCδ K376 mutant in cells treated with $M_4N$ and Rottlerin is statistically significant by t-test (5%). The difference between the control and the PKCδ in cells treated with $M_4N$ and Ly294002 is statistically significant by t-test (2%), B (67NR cells): The difference between the control and the PKCδ wild type in cells treated with $M_4N$ is statistically significant by t-test (5%). The difference between the control and the PKCδ K376 mutant in cells treated with $M_4N$ and Rottlerin is statistically significant by t-test (5%). The difference between the control and the PKCδ K376 mutant in cells treated with $M_4N$ and Ly294002 is statistically significant by t-test (2%). The difference between the control and the PKCδ in cells treated with $M_4N$ and Ly294002 is statistically significant by t-test (1%). C: Effect of Genistein (50 μM) on TUNEL-positive cell death induced by the combination treatment of $M_4N$ (80 μM) with Rottlerin (5 μM) or Ly294002 (20 μM) in 4T1 cells at 28 hrs after treatment. 'RoM' and 'LyM' designate the combination treatment of $M_4N$ with Rottlerin or Ly294002 respectively. Data are presented as means (+/−) SD in triplicates (A-C).

Direct evidence of PKCδ on induction of TUNEL-positive cell death by $M_4N$, Ro, and Ly. The data described above indicate that $M_4N$, Ro, and Ly modulate phosphorylation and cellular localization of PKCδ in both 4T1 and 67NR cells in less than 5 hrs after treatment. We next examined if there is a causal relationship between the action of PKCδ and cell death. We transfected PKCδ or PKCδ dominant negative (PKCδK376) vectors and vector alone (control) into either 4T1 or 67NR cells and examined the impact of these vectors on cell death induced by the drug treatments in combination with $M_4N$, Ro, and Ly. PKCδ dominant negative vectors are supposed to interfere in phosphorylation and nuclear translocation of PKCδ. As shown in FIG. 5, neither the control nor PKCδ dominant negative vectors had much effect on cell death in both 4T1 and 67NR cells without drug treatment. However, transfection of PKCδ vectors induced cell death in 4T1 cells even without drug treatment (FIG. 5A, (−)).PKCδ vectors induced cell death significantly in 4T1 cells but not in 67NR cells while vector alone (control) or PKCδK376 have little effect in induction of cell death in either 4T1 cells or 67NR cells (FIGS. 5A & 5B, (−)). Transfection of PKCδ vectors induced more cell death in both 4T1 and 67NR cells that were treated with $M_4N$ than transfection of control vectors (FIGS. 5A & 5B). Either Ro or Ly induced cell death synergistically with $M_4N$ in both 4T1 and 67NR cells that had been transfected with control vectors, in the same way as in the cells without transfection of any vectors (FIG. 5A). Transfection of PKCδ vectors induced more cell death in both 4T1 and 67NR cells that were treated with $M_4N$ plus Ro or $M_4N$ plus Ly than transfection of control vectors (FIGS. 5A & 5B). On the contrary, PKCδ dominant negative vectors (PKCδ K376) overall reduced the cell death induced by $M_4N$, $M_4N$ plus Ro, or $M_4N$ plus Ly treatment in both 4T1 and 67NR cells (FIGS. 5A & 5B). We have also examined the effect of Genistein (50 μM), known as the general Src tyrosine kinase inhibitor, on TUNEL-positive cell death induced by the combination treatment of $M_4N$ with either Ro or Ly in 4T1 cells (91). The data indicates that Genistein significantly suppressed the cell death (FIG. 5C).

Example 8

Figure 6:
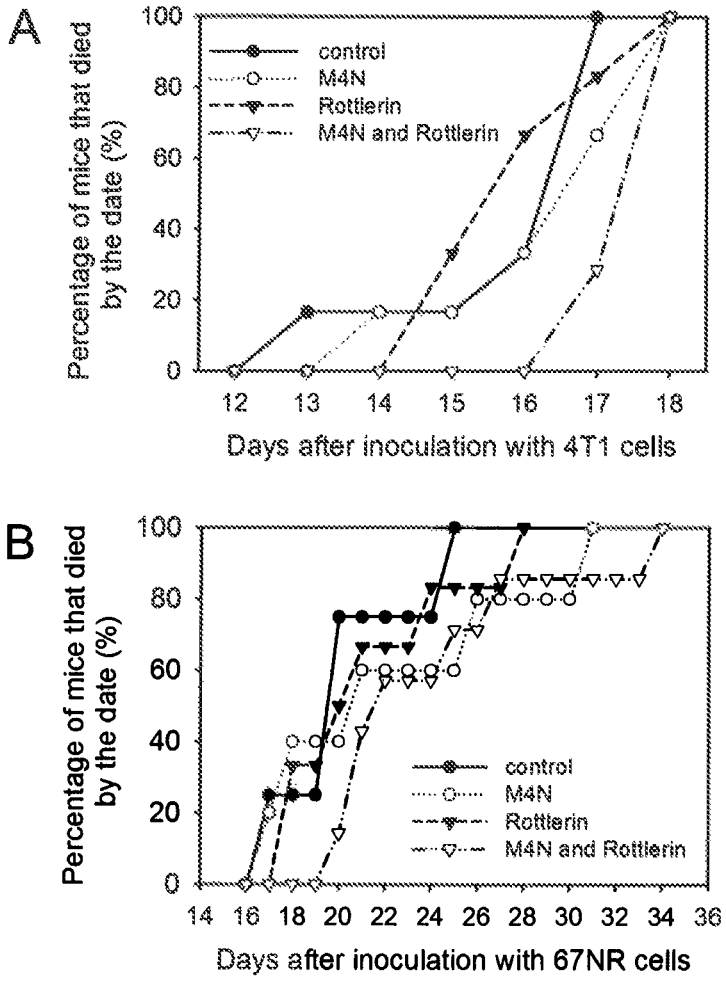
FIG. 6. Effect of $M_4N$ and Rottlerin on the survival time of 4T1 (A) and 67NR (B) tumor-bearing mice. A: $5\times10^4$ 4T1 cells were inoculated into fat pads of mammary glands in Balb/c female mice. The injections of either $M_4N$ (1 mg/shot) and Rottlerin (100 μg/shot) started 7 days after inoculation of tumors, Drug injections were performed three days a week. B: $5\times10^4$ 67NR cells were inoculated into fat pads of mammary glands in Balb/c female mice. The injections of either $M_4N$ (1 mg/shot) and Rottlerin (100 μg/shot) started 8 days after inoculation of tumors. Drug injections were performed three days a week. In either 4T1 or 67NR tumor-bearing mice there were five to six mice in each group. The percentage of mice that have died by the date after tumor inoculation was shown for each group.

Effect of combination treatment of $M_4N$ with Ro on the life-span and tumor sizes in Balb/c mice inoculated with either 4T1 or 67NR cells. Lastly, we examined if the benefit of the combination treatment by $M_4N$ with Ro can be applicable to the in vivo study. Ro has been safely administered to mice by intranasal instillations in other studies. In this study, we used intravenous injection of drugs instead of intranasal instillations using CPE (25/30) solvent system for both $M_4N$ and Ro. We first inoculated $5\times10^4$ of either 4T1 or 67NR cells into fat pads of mammary glands of Balb/c mice and examined if the drugs could elongate the life-span of these mice. We started to treat mice with drugs seven or eight days after the inoculation of 4T1 or 67NR cells respectively. We injected drugs three days a week after the initiation of drug treatment. Although either $M_4N$ or Ro alone didn't extend the life-span of 4T1-bearing mice, a combination treatment of $M_4N$ with Ro extended the life span of these mice (FIG. 6A). A similar tendency was found in mice inoculated with 67NR cells as well. As expected, mice overall survived longer with 67NR than 4T1 cell inoculations. While $M_4N$ or Ro alone didn't have much effect on the life-span of 67NR-bearing mice, a combination treatment of $M_4N$ with Ro overall extended the life span of the mice (FIG. 6B).

Example 9

Figure 7:
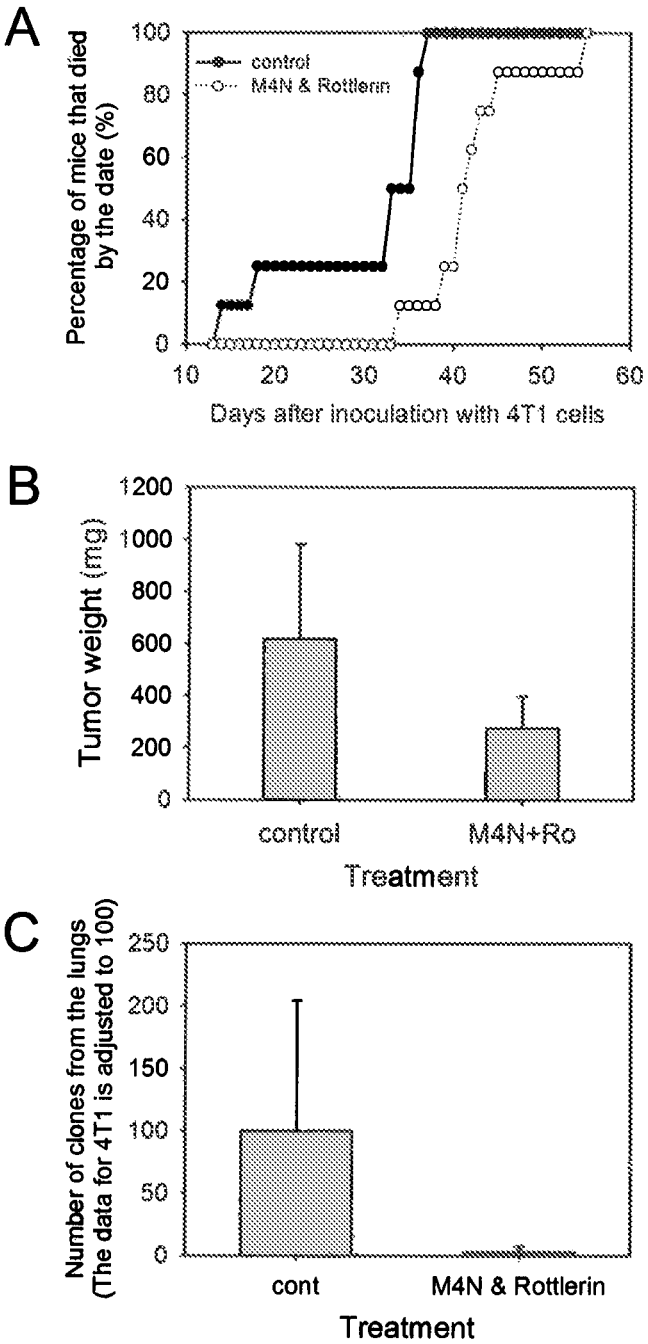
FIG. 7. Effect of combination treatment of $M_4N$ and Rottlerin on Balb/c mice inoculated with a small number of 4T1 tumor cells. $5\times10^3$ 4T1 cells were inoculated into fat pads of mammary glands in Balb/c female mice. Effect of combination treatment of $M_4N$ (1 mg/shot) and Rottlerin (100 μg/shot) was examined. Drug injections started 3 days after inoculation of tumors. Drugs were administered six days a week. A: The percentage of mice that have died by the date after tumor inoculation was shown for each group. B.

Since 4T1 cells are very aggressive and kill mice in only two or three weeks period under this experimental condition, we examined the effect of a combination treatment by $M_4N$ and Ro on mice inoculated with a smaller number of 4T1 cells with more extensive chemotherapy protocol. In the next experiment we inoculated only $5\times10^3$ cells instead of $5\times10^4$ cells into fat pads of mammary glands of Balb/c mice. And also we started to inject the drugs three days after the inoculation of the cancer instead of seven days and we injected drugs six days a week instead of three days a week. Even with $5\times10^3$ cells per fat pad, 4T1 cells killed all the mice without treatment only in 2 to 5.5 weeks after the inoculation of the cells. On the contrary, the first mouse among the treatment group died almost 5 weeks after the inoculation of the cells. Overall the combination treatment extended the life-span of mice about 12 days (FIG. 7A). The tumor size was compared at 18 days after the inoculation of the cancer between the control group and the treatment group. The data shows that the tumor size was significantly smaller in the treatment group than the control group (FIG. 7B).

Example 10

Effect of combination treatment of $M_4N$ with Ro on the metastasis to the lungs in Balb/c mice inoculated with 4T1 cells, measured by the clonogenicity assay. The clonogenicity assay was performed for the lungs from the mice either non-treated or treated with $M_4N$ plus Ro at 18 days after the inoculation of $5\times10^3$ 4T1 cells into fat pads. The validity of this assay was confirmed by the experiment to compare metastatic ability between 4T1 and 67NR cells (data not shown). The data shows that the lung metastasis was extremely small in treated mice while lung metastasis was already very prevalent in the control mice (FIG. 7C).

Example 11

Effect of $M_4N$, Ro, and Ly on the cell death and growth and the cellular localization of total PKCδ and phosphor-PKCδ ($Thr^{507}$) in LNCaP human prostate cancer cells. In the previous examples, we showed that Ro or Ly synergistically improved tumoricidal effect of $M_4N$ in mouse breast cancer cell lines, 4T1 and 67NR. Here we examined the effect of Ro and Ly on TUNEL-positive cell death induced by $M_4N$ in LNCaP human prostate cancer cells as an example for the application of the combination treatment to human cancer cells. As found in 4T1 and 67NR mouse breast cancer cells, either Ro or Ly synergistically augmented cell death induced by $M_4N$ in LNCaP cells while Ro or Ly alone has no effect (FIG. 8A) and cell death induced by $M_4N$ alone was also very small. On the other hand the MTT assay indicated that $M_4N$ treatment alone was able to reduce cell growth almost as much as a combination treatment of $M_4N$ with either Ro or Ly (FIG. 8B). A single treatment with either Ro or Ly also suppressed cell growth to some extent. In three cancer cell lines that we have studied so far, our data clearly indicated that although $M_4N$ alone was able to stop cancer cell growth, rapid cell death could be achieved only when $M_4N$ was used in combination with Ro and/or Ly (FIGS. 8A & B). We next examined the cellular localization of PKCδ and phosphor-PKCδ ($Thr^{507}$) in LNCaP cells treated with $M_4N$, Ro, and Ly for 5 hrs. Neither $M_4N$, Ro, nor Ly treatment caused any remarkable change in the expression of total PKCδ (FIG. 8C) However, the combination treatment of $M_4N$ with either Ro or Ly induced substantial increase in total PKCδ in the nuclei (FIG. 8C). The nuclear expression of phosphor-PKCδ ($Thr^{507}$) was augmented by either Ro or $M_4N$ treatment (FIG. 8D). A combination treatment of $M_4N$ with Ro induced more nuclear expression of phosphor-PKCδ ($Thr^{507}$) than either Ro or $M_4N$ single treatment (FIG. 8D). The extent of nuclear expression of PKCδ seems to be well correlated with the degree of the cell death under each condition (FIGS. 8A & 8C).

Example 12

Effect of combination treatment of $M_4N$ with Ly on the life-span in nude (nu/nu) mice orthotropically implanted with LNCaP tumors. In the accompanied paper we already showed that Ro improved the anti-cancer effect of $M_4N$ on mouse breast cancer cells. Here we applied the synergistic induction of cell death by $M_4N$ and Ly observed under tissue culture condition to the animal experiments, using human prostate cancer cell line LNCaP. Ly was already safely administered to mice intraperitoneally before (60, 6). In this study we administered $M_4N$ and Ly dissolved into the solution by using CPE (25/30) solvent system to mice intravenously (87). LNCaP tumors were orthotropically implanted into the vicinity of the prostate of nude mice. We started to treat the mice with a combination treatment of $M_4N$ and Ly eight days after the implantation of LNCaP cells. Some tumors started to appear under the skin, especially in the abdomen, for both control and treated mice. While these tumors appeared under the skin all over the body in the control group, they appeared only in the lower abdomen area in the mice treated with the combination (FIGS. 9 & 10). All the mice injected with only vehicles died between 38 and 53 days after the tumor implantation. On the contrary, all the mice injected with $M_4N$ and Ly survived at 76 days after the tumor implantation (FIG. 11A). The size of these tumors increased very rapidly in the control mice while it increased very slowly in the treated mice (FIG. 11B). All the control mice died of cancer in 5 to 8 weeks after tumor transplantation. Most of the mice from the control group already developed severe lung metastasis when they died (FIG. 11C, a-d). To compare the condition of the lung between the control and the treatment group, we killed some of the treated mice at 11 weeks after tumor transplantation. Unlike the lungs from the control group, those from the treatment group were devoid of obvious metastasis lesions (FIG. 11C, e-g). We examined the tumor lesions in the prostate region and those on the skin in the abdomen area in the treated mice that were killed at 11 weeks after tumor implantation. The pictures show the inside of the tumors that had been cut by the scalpel (FIG. 11D). In most of the tumor lesions there were cavities inside. The region inside the tumor capsules was filled with white connective-tissue like materials. We examined the histology of metastasis lesions in the lungs and the skins (FIG. 12). While we found very clear metastasis lesions in the lungs in 6 out of 8 control mice (FIG. 12A, a-h), we didn't find any metastasis lesions in the lungs of any mice treated with $M_4N$ and Ro (0 out of 4 mice) (FIG. 12A, i-l). While the tumors in the skins from the treated mice have large areas with lymphocyte infusions at their centers (FIG. 12B, i-l), those from the control mice only have very small areas with lymphocyte infusions (FIG. 12B, a-g).

Example 13

The tumors under the abdominal skin in the mice treated with $M_4N$ and Ly were small in the first 6 weeks (FIG. 10). However, the tumors increased in size after the first 6 weeks even with the treatment of $M_4N$ and Ly, We picked up one mouse (T8) to see if additional treatment with Ro might help to reduce the size of these tumors (FIG. 13). The treatment with $M_4N$, Ro, and Ly started at 9 weeks after the inoculation of tumors, Although the size of abdominal tumors was rapidly increasing between 6 and 9 weeks after the tumor inoculation, the tumors started to shrink very rapidly just after we changed the drug treatment from $M_4N$ and Ly combination to $M_4N$, Ro, and Ly combination (FIG. 13B).

Example 14

Dosage dependent effect of $M_4N$, Ro, and Ly on the cell death in LNCaP cells. We examined the effect of $M_4N$, Ro, and Ly on cell death in LNCaP cells at many different concentrations of these drugs. This is a necessary step for applying this combination treatment to clinical usage. The data shows that $M_4N$ induced cell death synergistically with either Ro or Ly in LNCaP cells in a very broad range of concentrations of the drugs (FIGS. 14A & B), Both Ro and Ly remained non-cytotoxic in tissue culture under this condition. The presence of either Ro or Ly made it possible for $M_4N$ to achieve great deal of cell death at lower concentrations of $M_4N$ than in the absence of it.

Example 15

Effect of Etoposide, Dichloroacetate, and Rapamycin on TUNEL-positive cell death induced by $M_4N$ in LNCaP cells. To explore other possible drugs to be combined with $M_4N$, we examined if Etoposide, Dichloroacetate, or Rapamycin can synergistically augment cell death with $M_4N$ (FIGS. 12, 15 & 16). We selected these drugs based on the speculations described in the introduction. The data indicates that either Etoposide, Dichloroacetate, or Rapamycin synergistically augmented TUNEL-positive cell death induced by $M_4N$ in 24 hrs, as predicted from their action on cellular metabolism (FIGS. 14C, D, E & F). A combination treatment of $M_4N$ (40 μM) with Rapamycin induced almost a hundred percent cell death in LNCaP cells at 48 hrs after treatment (FIG. 14F). This indicates that less than 40 μM $M_4N$ would be enough under clinical conditions for the treatment to be effective.

Example 16

Effect of combination treatment of $M_4N$ with either Ly, Ro plus Ly, Etoposide, or Rapamycin on the life-span and lung metastasis in nude (nu/nu) mice orthotropically implanted with LNCaP tumors. We applied the synergistic induction of cell death by $M_4N$ with either Ly, Ro plus Ly, Etoposide, or Rapamycin observed under tissue culture conditions to animal experiments (FIGS. 14 & 15). As in the previous experiment (FIGS. 9 to 13), in this study we administered $M_4N$, Ly, Ro, Etoposide, or Rapamycin to mice intravenously using CPE (25/30) solvent system (87). LNCaP tumors were orthotropically implanted into the vicinity of the prostate of nude mice as in the previous studies (FIGS. 9 to 13). However, in this experiment we implanted about eight times the volume of tumors as in the previous experiments to detect the difference of efficacy of various combination treatments much faster. We started to treat the mice with combination treatments three days after the implantation instead of eight days, considering that the tumor volume is already large at the time of implantation in this experiment. This allows less time for possible metastasis to the transplanted tumors in this experiment than in the previous one. All the control mice died by 21 days after implantation of LNCaP tumors. All the mice treated with Etoposide alone died by 24 days after the implantation while all the mice treated with $M_4N$ alone died by 33 days. The combination treatment of $M_4N$ with Ly improved the survival of tumor-bearing mice although all the mice eventually died by 51 days (FIG. 15A). This is an improvement compared with the survival time in the mice treated with either $M_4N$ or Ly alone. Three combination treatment of $M_4N$, Ro, and Ly improved survival rate greatly. All the mice except for one in this group (8 out of 9) survived beyond 70 days after the implantation (FIG. 15A). Meanwhile ail the mice treated with $M_4N$ and either Etoposide (9 out of 9) or Rapamycin (5 out of 5) survived beyond 70 days after the implantation (FIG. 15B). This is a great improvement compared with the survival time in the mice treated with either $M_4N$, Etoposide, or Rapamycin alone.

Example 17

Effect of the combination treatment on the lung metastasis (FIG. 15C). The lungs of the control mice very often showed massive metastatic lesions (4 out of 5). On the contrary, the lungs from the mice treated with the combination treatment of $M_4N$ with either Ro plus Ly or Etoposide did not show any obvious metastasis at 80 days after the tumor implantation (0 out of 5 and 0 out of 3 respectively). The lungs from the mice treated with either Etoposide alone, $M_4N$ alone, or $M_4N$ plus Ly showed some metastasis lesions (3 out of 5, 2 out of 4, and 2 out of 8 respectively). The data clearly showed that all Ly, Ro, and Etoposide had capability to improve anti-cancer activity of $M_4N$ against LNCaP cells in animal experiments.

Example 18

Effect of the combination treatment of $M_4N$ with either Ro or Rapamycin in various tissue culture cell lines. Lastly, we examined the combination effect of $M_4N$ with either Ro or Rapamycin in various tissue culture cells to see if these combination treatments are applicable to many tumor cells other than LNCaP cells. The data shows that the combination treatments effectively induce quick cell death in many tumor cell lines derived from various organs (FIGS. 16A & B).

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All references, including patents, websites, programs, databases and publications, mentioned in this specification are herein incorporated by reference to the same extent as if each independent patent and publication was specifically and individually indicated to be incorporated by reference.

REFERENCES

1. Megha, T., S, Lazzi, F. Ferrari, R. Vatti, C. M. Howard, G. Cevenini, L, Leonicini, P. Luzi, A. Giordano, and P. Tosi. 1999. Expression of the G2-M checkpoint regulators cyclin B1 and P34CDC2 in breast cancer: a correlation with cellular kinetics. Anticancer Res. 19:163-169,
2. Fang, F., and J. W. Newport. 1991. Evidence that the G1S and G2-M transitions are controlled by different cdc2 proteins in higher eukaryotes. Cell 66:731-742.
3. Dalton, S. 1992. Cell cycle regulation of the human cdc2 gene. The EMBO J. 11:1797-1804.
4. Morgan, D. O. 1995. Principles of cdk regulation. Nature 374:131-134.
5. Murray, A. W. 1992. Creative blocks: cell-cycle checkpoints and feedback controls. Nature 359: 599-604.
6. Kao, G. D., W. G. McKenna, and R. J. 1999, Muschel. P34(Cdc2) kinase activity is excluded from the nucleus during the radiation-induced G(2) arrest in HeLa cells. J. Biol. Chem. 274:34779-34784.
7. Ambrosini, G., C. Adida, and D. C. Altieri. 1997. A novel anti-apoptosis gene, surviving, expressed in cancer and lymphoma. Nat. Med. 3:917-921.
8. Deveraux, Q. L., and J. C. Reed. 1999. IAP family proteins-suppressors of apoptosis. Genes Dev. 13:239-252.
9. O'Connor, D.S., D. Grossman, J. Plescia, F. Li, H. Zhang, A. VIIIa, S. Tognin, P. C. Marschisio, and D. C. Altieri. 2000. Regulation of apoptosis at cell division by p34cdc2 phosphorylation of surviving. Proc. Natl. Acad. Sci. U.S.A. 97:13103-13107.
10. Grossman, D., J. M. McNiff, F. Li, and D.C. Altieri. 1999. Expression and targeting of the apoptosis inhibitor, survivin, in human melanoma. J. Invest. Dermatol. 113: 1076-1081.
11. Tamm, I., Y. Wang, E. SAusville, D. A. SCudiero, N. Vigna, T. Oltersdorf, and J. C. Reed. 1998. IAP-family protein surviving inhibits caspase activity and apoptosis induced by Fas (CD95), Bax, caspases, and anticancer drugs. Cancer Res. 58:5315-5320.
12. Hwu, J. R., W. N. Tseng, J. Gnabre, P. Giza, P, and R. C. Huang. 1998. Antiviral activities of methylated nordihydroguaiaretic acids. 1. Synthesis, structure identification, and inhibition of tat-regulated HIV transactivation. J. Med. Chem. 41:2994-3000.
13. Gnabre, J. N., J. N. Brady, D. J. Clanton, Y. Ito, J. Dittmer, R. B. Bates, and R. C. Huang. 1995. Inhibition of human immunodeficiency virus type 1 transcription and replication by DNA sequence-selective plant lignans. Proc. Natl. Acad, Sci. U.S.A. 92:11239-11243.
14. Chen, H., L, Teng, J. N. Li, R. Park, D. E. Moid, J. Gnabre, J. R. Hwu, W. N., Tseng, and R. C. Huang. 1998. Antiviral activities of methylated nordihydroguaiaretic acids, 2. Targeting helpes simplex virus replication by the mutation insensitive transcription inhibitor tetra-O-methyl-NDGA. J. Med. Chem. 41:3001-3007.
15. Craigo, J., M. Callahan, R. C. Huang, and A. L. DeLucia. 2000. Inhibition of human papillomavirus type 16 gene expression by nordihydroguaiaretic acid plant lignan derivatives. Antiviral Res. 47:19-28.
16. Heller, J. D., J. Kuo, T. C. Wu, W. M. Kast, and R. C. Huang, 2001. Tetra-O-methyl nordihydroguaiaretic acid induces G2 arrest in mammary cells and exhibits tumoricidal activity in vivo. Cancer Res. 61:5499-5504.
17. Chang, C. C., J. D. Heller, J. Kuo, and R. C. Huang. 2004. Tetra-O-methyl nordihydroguaiaretic acid induces growth arrest and cellular apoptosis by inhibiting Cdc2 and surviving expression. Proc. Natl. Acad. Sci. U.S.A. 101: 13239-13244.
18. Park, R., C. C. Chang, Y. C. Liang, Y. Chung, R. A. Henry, E. Lin, D. E. Mold, and R. C. Huang. 2005. Systemic treatment with tetra-O-methyl nordihydroguaiaretic acid suppresses the growth of human xenograft tumors. Clin. Cancer Res. 11:4601-4609.
19. Yeh, H.-C., C M. Puleo, T. C. Lim, Y.-P. Ho, P. E. Giza, R. C. C, Huang, and T.-H., Wang. 2006, A microfluidic-FCS platform for investigation on the dissociation of Spl-DNA complex by doxorubicin, Nucleic Acids Res. 34:e144.
20. Aslakson, C. J., and F. R. Miller. 1992, Selective events in the metastatic process defined by analysis of the sequential dissemination of subpopulation of a mouse mammary tumor. Cancer Res: 52:1399-1405.
21. Kikkawa, U., Y. Takai, Y Tanaka, R. Miyake, and Y, Nishizuka. 1983. Protein kinase C as a possible receptor protein of tumor-promoting phorbol esters, J. Biol. Chem. 258:11442-11445.

22. Kikkawa, U., A. Kishimoto, and Y. Nishizuka. 1989. The protein kinase C family; heterogeneity and its implications. Annu. Rev. Biochem. 58:31-44.

23. Jackson, D. N., and D. A. Foster, 2004. The enigmatic kinase Cδ: complex roles in cell proliferation and survival. FASEB J. 18:627-636, 24. Brodie, C, and P. M. Blumberg. 2003. Regulation of cell apoptosis by protein kinase Cδ. Apoptosis 8:19-27.

25. Steinberg, S. F. 2004, Distinctive activation mechanisms and functions for protein kinase Cδ, Biochem. J. 384:449-459.

26. Watanabe, T., Y. Ono, Y. Taniyama, K. Hazama, K. Igarashi, K. Ogita, U. Kikkawa, and Y. Nishizuka. 1992. Cell division arrest induced by phorbol ester in CHO cells over-expressing protein kinase C5 subspecies, Proc, Natl. Acad. Sci. U.S.A. 89:10159-10163.

27. Acs, P., M, Beheshti, Z. Szallasi, L. Li, S. H. Yuspa, and P.M. Blumberg. 2000. Effect of a tyrosine 155 to phenylalanine mutation of protein kinase Cδ on the proliferation and tumorigenic properties of NIH 3T3 fibroblasts. Carcinogenesis 21:887-891.

28. Stempka, L., A. Girod, H.-J. Muller, G. Rincke, F. Marks, M. Gschwendt, and D, Bossemeyer. 1997. Phosphorylation of protein kinase Cδ (PKCδ) at Threonine 505 is not a prerequisite for enzymatic activity. J. Biol. Chem. 272: 6805-6811.

29. Stempka, L., M, Schnolzer, S. Radke, G. Rincke, F. Marks, and M. Gschwendt. 1999. Requirements of protine kinase Cδ for catalytic function. J. Biol. Chem. 274:8866-8892.

30. Liu, Y., C. Graham, A. Li, R. J. Fisher, and S. Shaw, 2002. Phosphorylation of the protein kinase C-theta activation loop and hydrophobic motif regulates its kinase activity, but only activation loop phosphorylation is critical to in vivo nuclear-facor κB induction. Biochem, J. 361:255-265.

31. Liu. Y., N. V. Belkina, C. Graham, and S. Shaw. 2006. Independence of protein kinase C-δ activity from activation loop phosphorylation. Structural basis and altered functions in cells. J. Biol. Chem. 281:12102-12111.

32. DeVries, T. A., M. C. Neville, and M. E. Reyland. 2002. Nuclear import of PKCδ is required for apoptosis: identification of a novel nuclear import sequence. The EMBO J. 21:6050-6060, 33. DeVries-Seimon, T. A., A. M. Oiim, M. J., Humphries, and M. E. Reyland. 2007, Induction of apoptosis is driven by nuclear retention of protein kinase C delta. J, Biol, Chem. 282:22307-22314.

34. Emoto, Y., Y. Manome, G. Meinhardt, H. Kisaki, S. Kharbanda, M. Robertson, T. Gharyur, W. W. Wong, R. Kamen, R. Weichselbaum, and D. Kufe. 1995. Proteolytic activation of protein kinase C δ by an ICE-like protease in apoptotic cells. The EMBO J. 14:6148-6156.

35. Ghayur, T. M. Hugunin, R. V. Talanian, S, Ratnofsky, C, Quinlan, Y, Emoto, P. Pandey, R. Datta, Y, Huang, S. Kharbanda, H. Allen, R. Kamen, W. Wong, and D. Kufe. 1996. Proteolytic activation of protein kinase C delta by an ICE/CED 3-like protease induces characteristics of apoptosis. J, Exp. Med, 184:2399-2404, 36. Blass, M., I. Kronfeld, G. Kazimirsky, P. M. Blumberg, and C. Brodie. 2002. Tyrosine phosphorylation of protein kinase C8 is essential for its apoptotic effect in response to Etoposide. Mol. Cell. Biol. 22:182-195.

37. Yoshida, K., T. Yamaguchi, H. Shinagawa, N. Taira, K. I. Nakayama, and Y. Miki. 2006. Protein kinase C δ activates topoisomerase IIα to induce apoptotic cell death in response to DNA damage. Mol. Cell. Biol. 26:3414-3431.

38. Yang, J., S. A. Mani, J. L. Donaher, S. Ramaswamy, R. A. Itzykson, C. Come, P. Savaqner, I. Gitelman, A. Richardson, and R.A. Weinberg. 2004. Twist, a master regulator of morphogenesis, plays an essential role in tumor metastasis. Cell 117: 927-939.

39. Gordan, J. D., and M. C. Simon. 2007 Hypoxia-inducible factors: central regulators of the tumor phenotype. Curr. Opin, Genet. Dev. 17:71-77.

40. Werners, A., B. Pauweis, F. Lardon, F, and J. B. Vermorken, 2007. Review; implications of in vitro research on the effect of radiotherapy and chemotherapy under hypoxic conditions. Oncologists 12:690-712, 41. Melillo, G. 2007. Targeting hypoxia cell signaling for cancer therapy. 2007. Cancer Metastasis Rev. 26: 341-352.

42. Aldinucci, C, A. Carretta, L. Ciccoli, S. Leoncini, C. Signorini, G. Buonocore, and G. P. Pessina. 2007, Hypoxia affects the physiological behavior of rat cortical synaptosomes. Free Radic. Biol. Med. 42:1749-1756.

43. Clavijo. C, J.-L. Chen, K.-J. Kim, M. E. Reyland, and D. K. Ann. 2007. Protein kinase Cδ-dependent and -independent signaling in genotoxic response to treatment of desferoxamine, a hypoxia-mimetic agent. Am. J. Physiol. Cell Physiol. 292:C2150-C2160.

44. Serova, M, A. Ghoul, K. A. Benhadji, E. Cvitkovic, S. Faivre, F. Calvo, F. Lokiec, and E. Raymond. 2006. Preclinical and clinical development of novel agents that target the protein kinase C family. Seminars in Oncology 33:466-478.

45. Da Rocha, A. B., D. R. Mans, A. Regner, and G. Schwartsmann 2002. Targeting protein kinase C: New therapeutic opportunities against high-grade malignant gliomas? The Oncologist 7: 17-33.

46. Morgensztem, D., and H. L. McLeod. 2005. PI3K/Akt/mTOR pathway as a target for cancer therapy. Anticancer Drugs. 16:797-803.

47. Faivre, S., S. Djelloul, and E. Raymond. 2006. New paradigms in anticancer therapy: targeting multiple signaling pathways with kinase inhibitors. Semin. Oncol. 33:407-420.

48. Cully, M., H. You, A. J. Levine, and T. M. Mak. 2006. Beyond PTEN mutations: the PI3K pathway as an integrator of multiple inputs during tumorigenesis. Nature Rev. Cancer, 6:184-192.

49. Osaki, M., M. Oshimura, and H. Ito. 2004. PI3K-Akt pathway: Its function and alterations in human cancer. Apoptosis, 9:667-676.

50. Manning, B. D., and L. C. Cantley. 2007. Akt/PkB signaling: Navigating downstream. Cell 129:1261-1274.

51. Gschwendt, M., H. J. Muller, K. Kielbassa, R. Zang, W. Kittstein, G. Rincke, and F. Marks. 1994. Rottlerin, a novel protein kinase inhibitor. Biochem. Biophys. Res. Comm. 199:93-98.

52. Davies, S. P., H. Reddy, M. Caivano, and P. Cohen, 2000. Specificity and mechanism of action of some commonly used protein kinase inhibitors. Biochem, J, 351 (Pt 1):95-105.

53. Le Good, J. A., W. H. Ziegier, D. B. Parekh, D. R. Alessi, P. Cohen, and P. J. Parker. 1998, Protein kinase C isotypes controlled by phosphoinositide 3-kinase through the protein kinase PDK1. Science 281:2042-2045.

54. Jackson, D. N., and D. A. Foster, 2004. The enigmatic kinase Cδ: complex roles in cell proliferation and survival, PASEB J. 18:627-636.

55. Brodie, C, and P.M. Blumberg. 2003, Regulation of cell apoptosis by protein kinase Cδ. Apoptosis 8:19-27.
56. Steinberg, S. F. 2004. Distinctive activation mechanisms and functions for protein kinase Co. Biochem. J. 384: 449-459,
57. Tillman, D. M., K. Izeradjene, K. S. Szucs, L. Douglas, and J. A. Houghton. 2003, Rottlerin sensitizes colon carcinoma cells to tumor necrosis factor-related apoptosis-inducing ligand-induced apoptosis via uncoupling of the mitochondria independent of protein kinase C, Cancer Res. 63:5118-5125.
58. Kim, E.-H., S.-U. Kim, and K.-S. Choi. 2005. Rottlerin sensitized gloma cells to TRAIL-induced apoptosis by inhibition of Cdc-2 and the subsequent downregulation of surviving and XIAP. Oncogene 24:838-849.
59. Ringshausen, I., M. Oelsner, K. Weick, C. Bogner, C. Peschel, and T. Decker. 2006. Mechanisms of apoptosis-induction by rottlerin: therapeutic implications for B-CLL. Leukemia 20:514-520.
60. Hu, L., C. Zaloudek, G. B. Mills, J. Gray, and R. B. Jaffe. 2000, In vivo and in vitro ovarian carcinoma growth inhibition by a phosphatidylinositol 3-kinase inhibitor (LY294002). Clin. Cancer Res. 6:880-886.
61. Semba, S., N. Itch, M. Ito, M, Harada, and M. Yamakawa. 2002. The in vitro and in vivo effects of 2-(2-morpholinyl)-8-phenyl-chromone (LY294002), a specific inhibition of phosphatidylinositol 3'-kinase, in human colon cancer cells, Clin. Cancer Res. 8:1957-1963.
62. Berrie, C P, 2001. Phosphoinisitide 3-kinase inhibition in cancer treatment. Expert Opin. Investg. Drugs, 10: 1085-98.
63. Stein, R. C. 2001, Prospects for phosphoinositide 3-kinase inhibition as a cancer treatment. Endocr. Real. Cancer. 8: 237-48)
64. Eckhardt, B. L., B. S. Parker, R. K. van Laar, C M. Restall, A. L. Natoli, M. D. Tavaria, K. L. Stanley, E. K. Sloan, J. M. Moseley, and R. L. Anderson. 2005. Genomic analysis of a spontaneous model of breast cancer metastasis to bone reveals a role for the extracelluar matrix. Mol. Cancer. Res. 3:1-13.
65. Gordan, J. D., and M. C. Simon. 2007 Hypoxia-inducible factors: central regulators of the tumor phenotype. Curr. Opin. Genet. Dev. 17:71-77.
66. Manka, D., Z, Spicer, and D. E. Millhorn. 2005. Bcl-2/adenovirus E1B 19 kDa interacting protein-3 knockdown enables growth of breast, cancer metastases in the lung, liver, and bone. Cancer Res. 15:11689-11693.
67. Bonnet. S., S. L. Archer, J. Allalunis-Turner, A, Haromy, C. Beaulieu, R. Thompson. C. T, Lee, G. D. Lopaschuk, L. Puttagunta, S. Bonnet, G, Harry, K. Hashimoto, C. J. Porter, M. A. Andrade, B. Thebaud, and E. D. Michelakis. 2007. A mitochondria-$K^+$ channel axis is suppressed in cancer and its normalization promotes apoptosis and inhibits cancer growth. Cancer Cell 11:37-51.
68. Kroemer, G. & S. J. Martin. 2005. Caspase-independent cell death. Nature Med. 11:725-730.
69. Shizukuda, Y., A. Helisch, R. Yokota, and J. A. Ware. 1999. Downregulation of protein kinase Cδ activity enhances endothelial cell adaptation to hypoxia. Circulation 100:1909-1916.
70. Back, S.-H., U.-Y. Lee, E.-M. Park, M.-Y. Han, Y.-S., Lee. and Y.-M. Park. 2001. Role of protein kinase Cd in transmitting hypoxia signal to HSF and HIF-1. J. Cell. Phys. 188:223-235.
71. Conte, M., B. Soper, Q. Chang, and B. Tepperman. 2004. The role of PKCδ and PKCϵ in the neonatal rat colon in response to hypoxia challenge. Pediatric Res, 55:27-33.
72. Parekh, D. B., W. Ziegier, and P. J. Parker. 2000. Multiple pathways control protein kinase C phosphorylation. EMBO J. 19:496-503.
73. Newton, A. C. 2003. Regulation of the ABC kinases by phosphorylation; protein kinase C as a paradigm. Biochem J. 370 (Pt 2):361-371.
74. Rybin, V. O., A. Sabri, J. Short, J. C. Braz, J. D. Molkentin, and S. F. Steinberg. 2003. Cross-regulation of novel protein kinase C(PKC) isoform function in cardiomyocytes. J, Biol. Chem. 278:14555-14564.
75. Fukunaga, M., M. Oka, M. Ichihashi, T. Yamamoto, H. Matsuzaki, and U. Kikkawa. 2001. UV-induced Tyrosine phosphorylation of PKCδ and promotion of apoptosis in the HaCaT cell line. Biochem. Biophys. Res. Comm. 289: 573-579.
76. Parekh, D. B., R. M. Katso, N. R. Leslie, C. P. Dowries, K. J. Procyk, M D. Waterfield, and P. J. Parker. 2000. β1-Integral and PTEN control the phosphorylation of protein kinase C. Biochem. J. 352:425-433.
77. Kroemer, G., G. Lorenzo, and C. Brenner. 2007. Mitochondrial membrane permeabilization in cell death, Physiol. Rev. 87:99-163.
78. Parcel lier, A., L. A. Tintignac, E. Zhuravleva, and B. A. Hemmings 2008. PKB and the mitochondria: AKTing on apoptosis. Cellular Signal. 20:21-30.
79. Gupta, A. K., G. J. Cerniglia, R. Mick, M. S. Ahmed, V. J. Bakanauskas, R. J. Muschel, and W. G. Mckenna. 2003. Radiation sensitization of human cancer cells in vivo by inhibiting the activity of PI3K using Ly294002. Int. J. Radiation Oncol, Biol. Phys. 56:846-853.
80. Pulaski, B. A., and S, Ostrand-Rosenberg. 1998. Reduction of established spontaneous mammary carcinoma metastasis following immunotherapy with major histocompatibility complex class II and B7.1. Cancer Res. 58:1486-1493.
81. Vander Haar, E., S. I. Lee, S. Bandhakavi, T. J. Griffin, and D. H. Kim. 2007, Insulin signaling to mTOR mediated by the Akt/PKB substrate PRAS40. Nature Cell Biol, 9:316-323.
82. Mackintosh, C. 2004, Dynamic interactions between 14-3-3 proteins and phosphoproteins regulate diverse cellular processes. Biochem, J. 381:329-342.
83. Reuseh, H. P., S. Zimmermann, M. Schaefer, M. Paul, and K. Moelling. 2001. Regulation of Raf by Akt controls growth and differentiation in vascular smooth muscle cells. J. Biol. Chem. 276:33630-33637.
84. Chang, F., L. S. Steelman, J. T. Lee, J. G. Shelton, P. M. Navolanic, W. L. Blalock, R. A. Franklin, and J. A. McCubrey. 2003. Signal transduction mediated by the Ras/Raf/MEK/ERK pathway from cytokine receptors to transcription factors: potential targeting for therapeutic intervention. Leukemia 17:1263-1293.
85. Siddharth, K., V. Anautharam, Y. Yang, C. J. Choi, A. Kauthasamy, and A. G. Kauthasamy. 2005. Tyrosine phosphorylation regulated the proteolytic activation of protein kinase Cδ in dopaminergic neuronal cells. J. Biol. Chem. 280:28721-28730.
86. Li, T. K. and L. F. Liu. 2001. Tumor cell death induced by topoisomerase-targeting drugs. Ann. Rev. Pharmacol. Toxicol. 41:53-77.
87. Lopez, R. A., A. B. Goodman, M, Rhodes, J. A. Blomberg, and J. Heller. 2007. The anticancer activity of the transcription inhibitor terameprocol (meso-tetra-O-methyl nordihydroguaiaretic acid) formulated for systemic administration. Anti-Cancer Drugs 18:933-939.
88. Li, L., P. S. Lorenzo, K. Bogi, P. M. Blumberg, and S. H. Yuspa. 1999. Protein kinase Cδ targets mitochondria, alters mitochondrial membrane potential, and induces apoptosis in normal and neoplastic keratiocytes when overexpressed by an adenovirus vector. Mole. Cell. Biol. 19:8547-8558.

89. Wang, X., Z, Zili, J. Geller, and R. M. Hoffman. 1999. High-malignancy orthotopic nude mouse model of human prostate cancer LNCaP. The Prostate 39:182-186.

90. Chang C C, Liang Y C, Klutz A, Hsu C I, Lin C F, Mold D E, Chou T C, Lee Y C, Huang R C. 2006. Reversal of multidrug resistance by two nordihydroguaiaretic acid derivatives, $M_4N$ and maitose-M3N, and their use in combination with doxorubicin or paclitaxel. Cancer Chemotherapy Pharmacol 58:640-653.

91. Kaul S, Anautharam V, Yang Y, Choi C J, Kanthasamy A, and Kanthasamy A G. 2005 Tyrosine Phosphorylation Regulates the Proteolytic Activation of Protein Kinase C in Dopaminergic Neuronal Cells, J. Biol. Chem. 280: 28721-30

We claim:

1. A pharmaceutical anti-tumor composition comprising a synergistically effective amount of a derivative of nordihydroguaiaretic acid (NDGA) comprising [tetra-o-methyl] *tetra-O-methyl* nordihydroguaiaretic acid (M4N) or maltose-M3N and a synergistically effective amount of a metabolic modulator, wherein the metabolic modulator is selected from the group consisting of Ly294002, rottlerin, dichloroacetate, [and] rapamycin*, and the water soluble derivatives of rapamycin, everolimus and temsirolimus*.

2. A method of treating a tumor, comprising administering to a mammal having said tumor an effective amount of the pharmaceutical composition of claim 1.

3. The method of claim 2 wherein the tumor is selected from the group consisting of breast cancer, prostate cancer, lung cancer, colon cancer and ovarian cancer.

4. A method of inhibiting tumor growth in a mammal, said method comprising administering to said mammal a synergistically effective amount of a nordihydroguaiaretic acid (NDGA) derivative comprising [tetra-o-methyl] *tetra-O-methyl* nordihydroguaiaretic acid (M4N) or maltose-M3N; and a synergistically effective amount of a metabolic modulator, wherein the metabolic modulator is selected from the group consisting of Ly294002, rottlerin, dichloroacetate, [and] rapamycin*, and the water soluble derivatives of rapamycin, everolimus and temsirolimus*.

5. The method of claim 4 wherein the mammal is a human, cat, dog or mouse.

6. The method of claim 4 wherein the tumor is selected from the group consisting of breast cancer, prostate cancer, lung cancer, colon cancer and ovarian cancer.

*7. The method of claim 2 wherein the metabolic modulator is selected from: rapamycin, and the water soluble derivatives of rapamycin, everolimus and temsirolimus.*

*8. The method of claim 3 wherein the metabolic modulator is selected from: rapamycin, and the water soluble derivatives of rapamycin, everolimus and temsirolimus.*

*9. The method of claim 7 wherein the metabolic modulator is selected from: everolimus and temsirolimus.*

*10. The method of claim 9 wherein the metabolic modulator is everolimus.*

*11. The method of claim 4 wherein the metabolic modulator is selected from: rapamycin, and the water soluble derivatives of rapamycin, everolimus and temsirolimus.*

*12. The method of claim 11 wherein the metabolic modulator is selected from: everolimus and temsirolimus.*

*13. The method of claim 12 wherein the metabolic modulator is everolimus.*

*14. The method of claim 6 wherein the metabolic modulator is selected from: rapamycin, and the water soluble derivatives of rapamycin, everolimus and temsirolimus.*

* * * * *